US012702150B2

(12) United States Patent
Blotsky et al.

(10) Patent No.: US 12,702,150 B2
(45) **Date of Patent: *Aug. 11, 2026**

(54) METHODS AND COMPOSITIONS FOR SLOWING AN AGING PROCESS IN A HUMAN OR AN ANIMAL

(71) Applicant: Core Intellectual Properties Holdings, LLC, Goodyear, AZ (US)

(72) Inventors: Luke Blotsky, Goodyear, AZ (US); Krys Bojanowski, Goodyear, AZ (US)

(73) Assignee: Core Intellectual Properties Holdings, LLC, Goodyear, AZ (US)

( * ) Notice: Subject to any disclaimer, the term of this patent is extended or adjusted under 35 U.S.C. 154(b) by 1163 days.

This patent is subject to a terminal disclaimer.

(21) Appl. No.: 17/463,099

(22) Filed: Aug. 31, 2021

(65) Prior Publication Data

US 2022/0295855 A1 Sep. 22, 2022

Related U.S. Application Data

(63) Continuation of application No. 15/338,885, filed on Oct. 31, 2016, now Pat. No. 11,103,001.

(60) Provisional application No. 62/247,991, filed on Oct. 29, 2015.

(51) Int. Cl.

| | |
|---|---|
| ***A23L 33/29*** | (2016.01) |
| ***A23L 2/52*** | (2006.01) |
| ***A23L 33/10*** | (2016.01) |
| ***A23L 33/18*** | (2016.01) |
| ***A61K 31/19*** | (2006.01) |

(52) U.S. Cl.

CPC ................ *A23L 33/29* (2016.08); *A23L 2/52* (2013.01); *A23L 33/10* (2016.08); *A23L 33/18* (2016.08); *A61K 31/19* (2013.01)

(58) Field of Classification Search

CPC .......... A23L 33/10; A23L 33/29; A61K 31/19

See application file for complete search history.

(56) References Cited

U.S. PATENT DOCUMENTS

| | | | | |
|---|---|---|---|---|
| 6,579,544 B1 * | 6/2003 | Rosenberg | ............. | A61K 36/87 514/474 |
| 8,709,497 B2 * | 4/2014 | Blotsky | ................ | A61K 9/0007 424/617 |

FOREIGN PATENT DOCUMENTS

| | | | |
|---|---|---|---|
| WO | WO 2012097064 A1 * | 7/2012 | ............. A61K 31/19 |

OTHER PUBLICATIONS

Barbieri et al, J signal Transduction 2012, pp. 1-17. Article ID 982794 (Year: 2012).*

Internet Archive Wayback Machine webpage printout of "https://web.archive.org/web/20150906103710/https://lpi.oregonstate.edu/book/export/html/251", captured Sep. 6, 2015, pp. 1-20. Accessed Sep. 20, 2024. (Year: 2015).*

(Continued)

*Primary Examiner* — Rayna Rodriguez
*Assistant Examiner* — Janet L Coppins
(74) *Attorney, Agent, or Firm* — Noblitt & Newson, PLLC

(57) ABSTRACT

The present disclosure provides muscle regenerative compositions comprising an extracted mineral element composition, which slow the aging process. The disclosure provides methods of slowing an aging process in a human. For example, a method can comprise administering to a human or animal having an age-associated muscle wasting disorder an effective amount of a muscle regenerative composition comprising an extracted mineral element composition.

17 Claims, 2 Drawing Sheets

Specification includes a Sequence Listing.

‡ Mineral extract added in the amount indicated to nutritional drink.

* Indicates statistically significant change ($p<0.05$) versus nutritional drink without mineral extract.

(56) References Cited

OTHER PUBLICATIONS

Walston, Jeremy. Curr Opin Rheumatology 2012, vol. 6, pp. 623-627. (Year: 2012).*
Barbieri et al., "Reactive Oxygen Species in Skeletal Muscle Signaling," Journal of Signal Transduction (vol. 2012, Article ID 982794, pp. 1-17. (Year: 2012).
Aguiar et al., "Effects of Creatine Supplementation During Resistance Training on Myosin Heavy Chain (MHC) Expression in Rat Skeletal Muscle Fibers," Journal of Strength and Conditioning Research, vol. 24, No. 1, Jan. 2010, pp. 88-96.
Balagopal et al. "Effects of aging on in vivo synthesis of skeletal muscle myosin heavy-chain and sarcoplasmic protein in humans," 1997 the American Physiological Society, Downloaded from journals.physiology.org/journal/ajpendo (024.250.126.126) on May 27, 2020, pp. E790-E800.
Balagopal et al., "Age effect on transcript levels and synthesis rate of muscle MHC and response to resistance exercise," 2001 the American Physiological Society, Downloaded from journals.physiology.org/journal/ajpendo (024.250.126.126) on May 27, 2020, pp. E203-E208.
Bruce-Keller et al., "Bcl-2 Protects Isolated Plasma and Mitochondrial Membranes Against Lipid Peroxidation Induced by Hydrogen Peroxide and Amyloid ,B-Peptide," Journal of Neurochemistry, vol. 70, No. 1, 1998 , pp. 31-38.
Chen et al., "Senescence-like growth arrest induced by hydrogen peroxide in human diploid fibroblast F65 cells," Proc. Natl. Acad. Sci. USA 91 (1994), pp. 4130-4134.
Chen et al, "Superoxide is the major reactive oxygen species regulating autophagy," Cell Death and Differentiation (2009) 16, pp. 1040-1052.
Deneau et al., "Anti_Diabetic Activity f a Mineraloid Isolate, in vitro and in Genetically Diabetic Mice," Int. J. Vitam. Nutr. Res., 81 (1), 2011, pp. 34-42.
Hansen et al., "A reducing redox environment promotes C2C12 myogenesis—implications for regeneration in aged muscle," Cell Biol Int. Jun. 2007 ; 31(6): pp. 546-553.
Kamaruddin et al., "Cytoprotective Role of Omentin Against Oxidative Stress-Induced Vascular Endothelial Cells Injury," Molecules 2020, 25, 2534, www.mdpi.com/journal/molecules pp. 1-13.
Powers et al., "Exercise-Induced Oxidative Stress: Cellular Mechanisms and Impact on Muscle Force Production," Physiol Rev. Oct. 2008 ; 88(4): pp. 1243-1276.
Nose et al., "Transcriptional activation of early-response genes by hydrogen peroxide in a mouse osteoblastic cell line," Bur. J. Biochem. 201, pp. 99-106 (1991).
Borg et al, Differences in Nutrient Intake and Biochemical Nutrient Status Between Sarcopenic and Nonsarcopenic Older Adults—Results From the Maastricht Sarcopenia Study, JAMDA 17 (2016) 393e401.
Verlaan et al., Nutritional status, body composition, and quality of life in community dwelling sarcopenic and non-sarcopenic older adults: A case-control study, Clinical Nutrition 36 (2017) 267e274.
Cruz-Jentoft et al., Sarcopenia: European consensus on definition and diagnosis Report of the European Working Group on Sarcopenia in Older People, Age and Ageing 2010; 39: 412-423.
Fiatarone et al., Exercise Training and Nutritional Supplementation for Physical Frailty in Very Elderly People, The New England Journal of Medicine, Jun. 23, 1994, vol. 330, No. 25.
Oh et al., Age- and sex-related differences in myosin heavy chain isoforms and muscle strength, function, and quality: a cross sectional study, J Exerc Nutrition Biochem. 2018;22(2):043-050.
Irwin H. Rosenberg, Sarcopenia: Origins and Clinical Relevance, Clin Geriatr Med 27 (2011) 337-339.
Timmerman et al., A moderate acute increase in physical activity enhances nutritive flow and the muscle protein anabolic response to mixed nutrient intake in older adults, Am J Clin Nutr 2012;95:1403-12.

* cited by examiner

‡ Mineral extract added in the amount indicated to nutritional drink.

* Indicates statistically significant change ($p<0.05$) versus nutritional drink without mineral extract.

‡ Mineral extract added in the amount indicated to nutritional drink.

* Indicates statistically significant change ($p<0.05$) versus nutritional drink without mineral extract.

METHODS AND COMPOSITIONS FOR SLOWING AN AGING PROCESS IN A HUMAN OR AN ANIMAL

RELATED APPLICATIONS

The present application is a continuation patent application of U.S. patent application Ser. No. 15/338,885, entitled "Methods and Compositions for Modulating Muscle and Bone Loss", filed on Oct. 31, 2016, which claims the benefit of and priority to U.S. Provisional Patent Application No. 62/247,991, filed Oct. 29, 2015, which are incorporated herein in its entirety.

REFERENCE TO A SEQUENCE LISTING SUBMITTED AS A TEXT FILE VIA EFS-WEB

The Sequence Listing submitted Jun. 3, 2022 as a text file named "106600117 ST25.txt," created on Jun. 3, 2022, and having a size of 4 Kb, is hereby incorporated by reference pursuant to 37 C.F.R. $1.52(e)(5). In addition, the Sequence Listing submitted Oct. 31, 2016 as a text file named "31598_113026_ST25.txt," created on Oct. 28, 2015, and having a size of 3,553 bytes, is hereby incorporated by reference pursuant to 37 C.F.R. § 1.52(e)(5).

TECHNICAL FIELD

The present disclosure relates to methods and compositions used to modulate muscle and bone mass, e.g., to slow, reduce, delay, treat or prevent muscle and/or bone loss and related pathologies in humans and animals.

BACKGROUND

Decline in muscle mass and contractile function (sarcopenia or muscle wasting) and gradual or rapid bone loss are prominent features of human aging. As one ages, muscles degenerate and disappear at an accelerating rate, reaching 1% per year about age of 65. This has tremendous impact both on body fitness (motility, lifestyle) and appearance (ex. sagging face). The cost of treating sarcopenia-related health issues in the United States has been estimated at $20-30 billion (Balagopal et al., 1997). Sarcopenia is an involuntary decline in lean muscle mass, strength and function, it increases the risk of loss of functional capacity in the elderly, and is not necessarily related to a disease state.

In contrast to age-related muscle loss, severe weight loss and in particular muscle wasting is a serious phenomenon that occurs on a broad scale in patients suffering from diseases, disorders and trauma. Muscle wasting in chronic disease is defined as an involuntary loss of body weight of more than 5% within one month. If loss of lean body mass occurs at a more gradual rate but during a longer period, the wasting may be referred to as chronic muscle wasting. Muscle wasting may be observed during recovery of trauma or surgery, whereas severe muscle wasting may be observed in diseases such as cancer, AIDS, COPD, diabetes mellitus and heart failure. The rate of muscle wasting is associated with increased morbidity and mortality. The cause of muscle wasting as a result of a disease is thought to be multifactorial. Muscle wasting can also be caused by malnourishment, in particular protein-energy malnourishment. In particular the latter type of malnourishment can be treated or prevented by providing extra protein or energy sources.

Bone mass evolves throughout life and is thought to be regulated by genetic, mechanical and hormonal mechanisms. Bone mineral acquisition occurs during childhood and peak bone mass is achieved around 20 years of age. During this period, bone formation exceeds bone resorption. Later in life, and particularly around the time of menopause, or in the elderly, bone mass and quality are impaired due to a higher bone turnover with excessive bone resorption leading to a gradual loss of bone mass, microarchitecture, structure and strength. To maintain bone, it is important to restore the balance between bone formation and bone resorption. This bone remodeling process is regulated at the bone cell level involving a tight interaction between bone forming cells (osteoblasts) and bone resorbing cells (osteoclasts).

What is needed are methods and compositions to modulate, muscle and bone mass, e.g., to slow, reduce, delay, treat or prevent muscle and/or bone loss and related pathologies in humans and animals.

SUMMARY

Figure 1:
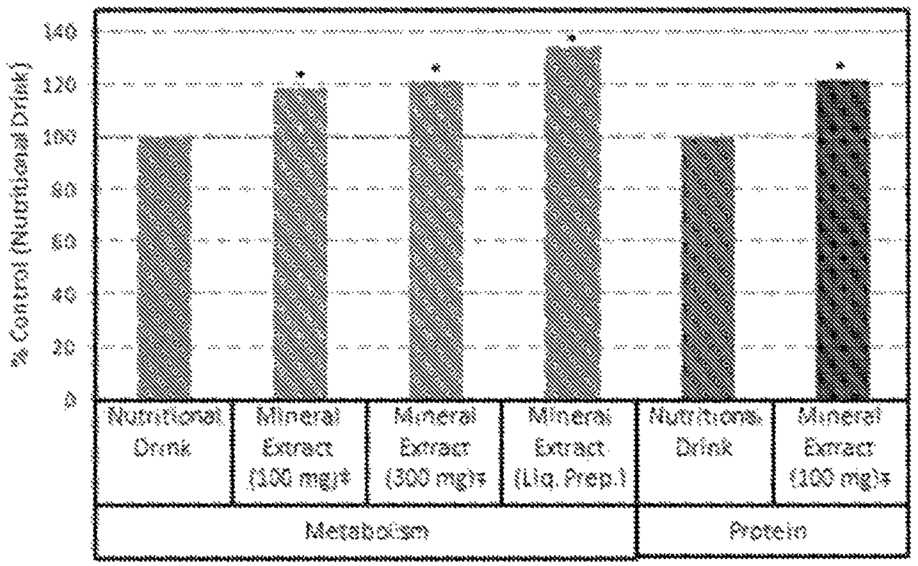
FIG. 1 shows representative data for human skeletal muscle cells ("HSkMC") exposed to nutritional drink with the indicated amounts of an extracted mineral element composition compared to nutritional drink without of an extracted mineral element composition. The data show the effect on metabolic activity and insoluble protein as indicated in the figure. All data are plotted as normalized values compared to the response in cells exposed to nutritional drink without of an extracted mineral element composition (i.e., the 100% control level).

The present disclosure comprises methods and compositions to modulate, muscle and bone mass, e.g., to slow, reduce, delay, treat or prevent muscle and/or bone loss and related pathologies in humans and animals. An aspect of modulating muscle and or bone mass comprises increasing protein synthesis to aid in increased bone and/or muscle mass. Compositions of the present disclosure comprise an extracted mineral element composition and compositions comprising an extracted mineral element composition that are useful to modulate, muscle and bone mass, e.g., to slow, reduce, delay, treat or prevent muscle and/or bone loss in humans or animals, and methods for modulating, slowing, reducing, delaying treating, or preventing muscle and/or bone loss and treating or ameliorating physical conditions related to bone and/or muscle loss. Compositions of the present disclosure comprise an extracted mineral element composition and compositions comprising an extracted mineral element composition. Methods of the present disclosure comprise methods of modulating, slowing, reducing, delaying treating, or preventing muscle loss conditions comprising administering an effective amount of an extracted mineral element composition in a liquid or solid form, for example, in a nutritional drink or foodstuff, or a capsule formulation, to modulate, muscle and bone mass, e.g., to slow, reduce, delay, treat or prevent muscle loss occurring in a human or animal. Methods of the present disclosure comprise methods of modulating, slowing, reducing, delaying treating, or preventing bone loss conditions comprising administering an effective amount of an extracted mineral element composition in a liquid or solid form, for example, for example, in a nutritional drink or foodstuff, or a capsule formulation, to modulate, muscle and bone mass, e.g., to slow, reduce, delay, treat or prevent bone loss occurring in a human or animal.

An extracted mineral element composition is provided or administered to subjects, humans or animals, alone or in combination with other components, to form muscle and/or bone loss modulating compositions. For example, an extracted mineral element composition of the present disclosure may be combined with a foodstuff or beverage to provide a muscle and/or bone loss modulating composition that is consumed by the subject. An extracted mineral element composition may be provided in capsular form with other components, such as vitamins, and may include pharmaceutical excipients and diluents. Effective amounts of muscle and/or bone loss modulating compositions are administered, for example, to inhibit or modulate the degeneration of muscles, muscle cells and/or contractile muscle fibers, to enhance myeloblast differentiation into mature muscle fibers, or to inhibit bone resorption or enhance bone cell (e.g., osteoblast) activity for bone formation, and to ameliorate, prevent or treat conditions related to muscle and/or bone loss conditions in the body. Muscle loss conditions include, but are not limited to, a decrease in the mass of the muscle which may be partial or complete wasting away of muscle, muscle weakness, and may be a co-morbidity of several common diseases, including cancer, AIDS, congestive heart failure, COPD (chronic obstructive pulmonary disease), renal failure, and severe burns; and cachexia. Bone loss conditions, include, but are not limited to, decrease in bone mass, low activity by osteoblast cells, high activity by osteoclast cells, osteoporosis, or fracture, and may be a co-morbidity with autoimmune disorders, rheumatoid arthritis, lupus, multiple sclerosis, ankylosing spondylitis, celiac disease, inflammatory bowel disease, weight loss surgery including gastric bypass, gastrectomy, gastrointestinal bypass procedures, endocrine and hormonal disorders, diabetes, hyperthyroidism, hyperparathyroidism, Cushing syndrome, thyrotoxicosis, irregular menses, premature menopause, testosterone and estrogen levels in men, leukemia, lymphoma, multiple myeloma, sickle cell disease, blood and bone marrow disorders, thalassemia, stroke, Parkinson's disease, spinal cord injuries, depression, eating disorders such as anorexia nervosa, cancer, breast cancer, prostate cancer, chronic obstructive pulmonary disease (COPD), AIDS/HIV, female athlete triad, kidney disease, liver disease, organ transplants, polio and post-polio syndrome, poor diet, scoliosis, and weight loss.

Compositions of the present disclosure comprise an extracted mineral element composition and compositions comprising an extracted mineral element composition, for example, in a composition ingestible by humans or animals, for muscle and/or bone loss modulating compositions.

DETAILED DESCRIPTION

The present disclosure comprises compositions and methods of treating, reducing, or preventing complications and pathologies of conditions related to muscle and/or bone loss.

Age-related involuntary loss of muscle mass, bone mass and strength occurs during aging. Regarding the degenerative loss of skeletal muscle mass, it occurs at a rate of 3-8% per decade after the age of 30 years and accelerates from 60 years of age. Both impaired muscle mass and muscle strength relate to age-related loss of muscle function. The major drivers for maintenance of skeletal muscle mass are the stimulation of muscle protein synthesis and the inhibition of muscle protein breakdown. Muscle protein synthesis is stimulated by the bioavailability of amino acids (for example, leucine) and physical activity. Both contribute to a positive net muscle protein balance (i.e. difference between muscle protein synthesis and protein breakdown). Compositions and methods of the present disclosure maintain muscle mass and prevent muscle decline and muscle wasting. Protein starvation and muscle inactivity, which often occur with ageing and disease, result in a failure to maintain muscle mass, with muscle wasting. With aging, an imbalance exists between muscle protein synthesis and breakdown. The anabolic response to lack of food intake or absorption may further contribute to an insufficient net muscle protein synthesis, and result in the subsequent muscle decline seen with aging. Compared to younger adults, the elderly may need higher levels of amino acids, for example, leucine, to stimulate muscle protein synthesis. Reduced responsiveness of muscle that occurs in elderly is called anabolic resistance which leads to muscle decline. Many disease states may create nutritional states mimicking anabolic resistance or result in reduced absorption of amino acids, resulting in muscle wasting and reduction in strength and agility.

Bone mineral density (BMD) decreases with age in both males and females. Decreased amounts of bone mineral content (BMC) and BMD correlate with decreased bone strength and predispose patients to fracture. Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes one to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the life-cycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

Methods of the present disclosure comprise providing an effective amount of an extracted mineral element composition, or a composition comprising an extracted mineral element composition, to a human or animal to modulate, muscle and bone mass, e.g., to slow, reduce, delay, treat or prevent muscles wasting. Methods of the present disclosure comprise providing an effective amount of an extracted mineral element composition, or a composition comprising an extracted mineral element composition to a human or animal to modulate muscle and bone mass, e.g., treat, enhance, or increase muscle mass. As used herein, muscle wasting refers to a progressive loss of muscle mass and/or to the progressive weakening and degeneration of muscles, including the skeletal or voluntary muscles, which control movement, cardiac muscles, which control the heart (cardiomyopathies), and smooth muscles. Chronic muscle wasting is a chronic condition (i.e. persisting over a longer period of time) characterized by progressive loss of muscle mass, weakening and degeneration of muscle.

The loss of muscle mass that occurs during muscle wasting may be due to muscle protein degradation by catabolism. Protein catabolism occurs because of an unusually high rate of protein degradation, an unusually low rate of protein synthesis, or a combination of both. Muscle protein catabolism, whether caused by a high degree of protein degradation or a low degree of protein synthesis, leads to a decrease in muscle mass and to muscle wasting.

Methods of the present disclosure comprise providing an effective amount of an extracted mineral element composition, or a composition comprising an extracted mineral element composition, to a human or animal to modulate, muscle and bone mass, e.g., to slow, reduce, delay, treat or prevent muscles wasting associated with chronic, neurological, genetic or infectious pathologies, diseases, illnesses or conditions, including, but not limited to, muscular dystrophies such as duchenne muscular dystrophy and myotonic dystrophy; muscle atrophies such as post-polio muscle atrophy (PPMA); cachexias such as cardiac cachexia, AIDS cachexia and cancer cachexia, malnutrition, leprosy, diabetes, renal disease, chronic obstructive pulmonary disease (COPD), cancer, end stage renal failure, sarcopenia, emphysema, osteomalacia, HIV infection, AIDS, and cardiomyopathy. In addition, methods of the present disclosure comprise providing an effective amount of an extracted mineral element composition to a human or animal to modulate, muscle and bone mass, e.g., to slow, reduce, delay, treat or prevent muscles wasting related to conditions related to muscle wasting, including but not limited to, chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism.

Muscle wasting, if not stopped, can have health consequences. For example, the changes that occur during muscle wasting can lead to a weakened physical state that is detrimental to an individual's health, resulting in increased susceptibility to infraction and poor performance status. In addition, muscle wasting is a strong predictor of morbidity and mortality in patients suffering from cachexia and HIV/AIDS.

Burns result in a testosterone reduction, nitrogen level reduction and a reduction in bone mineral density (BMD), which may persist even as long one year following the injury and is associated with impaired wound healing, increased infection risks, erosion of lean body mass, hampered rehabilitation, and delayed reintegration of burn survivors into society. Catabolic effects initiated as a result of the burn lead to significant involuntary weight loss, further compounding the problem.

Spinal cord injuries may result in the alteration central neurotransmitter secretion or production, which in turn may cause a hypothalamus-pituitary-adrenal axis dysfunction, leading to decreases in testosterone and other hormone levels. Spinal cord injury or other acute illness or trauma characteristically includes heightened catabolism in conjunction with the lowered anabolic activity resulting in a condition that is prone to loss of lean body tissue. As long as the catabolic process goes uninterrupted, disturbed nutrient utilization will continue. The effects of the loss of lean body mass include the development of wounds and impaired healing mechanisms.

In an embodiment, a method of treating, reducing the incidence of, delaying progression of, reducing the severity of, or alleviating symptoms associated with a muscle wasting disorder in a subject, comprises the step of administering to the subject an effective amount of an extracted mineral element composition, or a composition comprising an extracted mineral element composition, in an amount effective to treat the muscle wasting disorder in said subject. According to an aspect, a muscle wasting disorder is due to a pathology, illness, disease or condition. In an embodiment, the pathology, illness, disease or condition is neurological, infectious, chronic or genetic. In an embodiment, the pathology, illness, disease or condition is a muscular dystrophy, a muscular atrophy, x-linked spinal-bulbar muscular atrophy (SBMA), a cachexia, malnutrition, leprosy, diabetes, renal disease, chronic obstructive pulmonary disease (COPD), cancer, end stage renal failure, sarcopenia, emphysema, osteomalacia, HIV infection, AIDS, or cardiomyopathy. In an embodiment, the muscle wasting disorder is an age-associated muscle wasting disorder; a disuse deconditioning-associated muscle wasting disorder; or the muscle wasting disorder is due to chronic lower back pain; burns; central nervous system (CNS) injury or damage; peripheral nerve injury or damage; spinal cord injury or damage; chemical injury or damage; or alcoholism.

Methods of the present disclosure comprise providing an effective amount of an extracted mineral element composition, or a composition comprising an extracted mineral element composition, to a human or animal to modulate, muscle and bone mass, e.g., to slow, reduce, delay, treat or prevent bone loss. Methods of the present disclosure comprise providing an effective amount of an extracted mineral element composition, or a composition comprising an extracted mineral element composition, to a human or animal to treat a bone mass loss-related disorder in a subject. Methods of the present disclosure comprise providing an effective amount of an extracted mineral element composition, or a composition comprising an extracted mineral element composition, to a human or animal to modulate bone mass, e.g., to increase, promote, stimulate, treat or enhance bone formation in a subject. Methods of the present disclosure comprise providing an effective amount of an extracted mineral element composition, or a composition comprising an extracted mineral element composition, to a human or animal to modulate bone mass, e.g., to increase, promote, stimulate, treat or enhance increasing bone mass in the human or animal subject.

Methods of the present disclosure comprise providing an effective amount of an extracted mineral element composition, or a composition comprising an extracted mineral element composition, to a subject, human or animal, to modulate, muscle and bone mass, e.g., to slow, reduce, delay, treat or prevent bone mass loss. Bone mass loss may be due to osteoporosis, osteopenia, increased bone resorption, bone fracture, bone frailty, loss of bone mineral density (BMD), or any combination thereof. Methods of the present disclosure comprise providing an effective amount of an extracted mineral element composition, or a composition comprising an extracted mineral element composition, to a subject, human or animal, to modulate treat, promote, stimulate, enhance, or increase bone mass gain. In an embodiment, a method increases the strength of a bone of a subject. In an embodiment, a method stimulates or enhances osteoblastogenesis, or an embodiment the method inhibits osteoclast proliferation.

Methods of the present disclosure include administering an effective amount of a composition comprising an extracted mineral element composition to modulate, muscle and bone mass, e.g., to slow, reduce, delay, treat or prevent osteoporosis. "Osteoporosis" refers to a thinning of the bones with reduction in bone mass due to depletion of calcium and bone protein or a systemic skeletal disease, characterized by low bone mass and deterioration of bone tissue, with a consequent increase in bone fragility and susceptibility to fracture. In osteoporotic patients, bone strength is abnormal, with a resulting increase in the risk of fracture. Osteoporosis may deplete both the calcium and the protein collagen normally found in the bone, resulting in either abnormal bone quality or decreased bone density. Bones that are affected by osteoporosis can fracture with only a minor fall or injury that normally would not cause a bone fracture. The fracture can be in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility. Osteoporosis can result from androgen deprivation, can be primary or secondary osteoporosis, or is postmenopausal osteoporosis, juvenile osteoporosis, idiopathic osteoporosis, or senile osteoporosis.

Methods of the present disclosure comprise providing an effective amount of an extracted mineral element composition, or a composition comprising an extracted mineral element composition, to a human or animal to modulate, muscle and bone mass, e.g., to slow, reduce, delay, treat or prevent bone mass loss, increase bone mineral density (BMD); increase bone mass; increase bone strength; improve bone function; decrease fracture risk; or improve exercise tolerance.

Methods of the present disclosure comprise providing an effective amount of an extracted mineral element composition, or a composition comprising an extracted mineral element composition, to a human or animal to modulate, muscle and bone mass, e.g., to slow, reduce, delay, treat or prevent or reduce the risk of developing a skeletal-related event (SRE), such as bone fractures, surgery of the bone, radiation of the bone, spinal cord compression, new bone metastasis, bone loss, or a combination thereof.

A skeletal-related event may comprise fractures, including but not limited to, pathological fractures, non-traumatic fractures, vertebral fracture, non-vertebral fractures, morphometric fractures, or a combination thereof. Fractures may be simple, compound, transverse, greenstick, or comminuted fractures. Fractures may be to any bone in the body, or any one or more bones, for example, of the arm, wrist, hand, finger, leg, ankle, foot, toe, hip, collar bone, or a combination thereof. Methods disclosed herein may be used in treatment, prevention, suppression, inhibition or reduction of the risk of skeletal-related events such as pathologic fractures, spinal cord compression, hypercalcemia, bone-related pain, or their combination.

Skeletal-related events may comprise the necessity for bone surgery and/or bone radiation, for the treatment of pain resulting from bone damage, or nerve compression, spinal cord compression, or the necessity for changes in antineoplastic therapy, including changes in hormonal therapy, bone metastases, or bone loss.

Methods of the present disclosure may comprise administration of compositions disclosed herein along with other treatments that increase muscle mass or activity and/or bone mass. The administration of compositions may precede, occur at or near the same time as, or follow, such other treatments. For example, other treatments may include exercise or weight-bearing exercise. Muscle atrophy may be opposed by the signaling pathways which induce muscle hypertrophy, or an increase in muscle size. Therefore one way in which exercise induces an increase in muscle mass is to down-regulate the pathways which have the opposite effect. Disuse atrophy occurs from a lack of physical exercise. In most people, muscle atrophy is caused by not using the muscles enough. People with sedentary jobs, medical conditions that limit their movement, or decreased activity levels can lose muscle tone and develop atrophy. This type of atrophy may aided by compositions and methods of the present disclosure and exercise. Bedridden people can have significant muscle wasting as do astronauts who are away from the Earth's gravity can develop decreased muscle tone.

An Extracted Mineral Element Composition

Compositions of the present disclosure comprise an extracted mineral element composition. The method of making an extracted mineral element composition is taught in U.S. Pat. No. 8,709,497 and compositions claimed in U.S. Pat. No. 9,044,417, and U.S. patent application Ser. No. 14/717,660; each of which is herein incorporated in its entirety. Briefly, to make an extracted mineral element composition of the present disclosure, a soil from a suitable site, comprising the elements as described in U.S. Pat. No. 8,709,497, is collected and subjected to the aqueous extraction process described therein to produce a liquid extracted mineral element composition containing mineral elements which may be dried to produce a dry powder extracted mineral element composition.

As described in U.S. Pat. No. 8,709,497, an extracted mineral element composition is produced by the procedures described herein may comprise a minimum of 8 macro mineral elements and a minimum of 60 micro mineral elements. Similarly, an extracted mineral element composition produced by the procedures described herein may consist essentially of a minimum of 8 macro mineral elements and a minimum of 60 micro mineral elements. Both the liquid an extracted mineral element composition and dry powder an extracted mineral element composition may comprise an extracted mineral element composition described herein.

Physical testing and analysis was also conducted on the liquid and dry mineral element compositions. Typical specifications of the liquid an extracted mineral element composition range in color and may be from yellow to amber brown, and contain between 1 to 10% by weight of mineral elements, or from 3-5% by weight of mineral elements. The liquid an extracted mineral element composition is acidic with a pH ranging from 2.5-4.5, or from 2.5-3.5. The liquid an extracted mineral element composition can be dried to produce an anhydrous powder. The anhydrous powder may range in color from light-off-white to brown, or from yellow to golden amber, is insoluble in non-polar solvents such as hydrophobic liquids (oil and fats), is insoluble in alcohol, and is readily soluble, yet non-swelling, in water and hydro-alcoholic solutions at concentrations of 1 to 5% by weight, or at concentrations of 3-5% by weight. The dry powder is partially soluble or capable of being partially suspended in polar solvent in supersaturated solutions.

Both liquid and dry extracted mineral element compositions are produced by the procedures described herein and may comprise a minimum of 8 macro mineral elements and a minimum of 60 micro mineral elements as described in U.S. Pat. No. 8,709,497. Similarly, both liquid and dry extracted mineral element compositions produced by the procedures described herein may consist essentially of a minimum of 8 macro mineral elements and a minimum of 60 micro mineral elements as described in U.S. Pat. No. 8,709,497. The micro mineral elements include trace and rare earth mineral elements.

For example, the dry an extracted mineral element composition may comprise concentrations ranging from 0.0001-20.00% by weight percent, from 0.001%-10%, from 0.1% to 20%, from 1% to 20%, from 1% to 10%, from 5% to 10%, from 10-20%, from 10% to 15%, from 15% to 20%, from 1% to 5%, from 5% to 15%, by weight percent, the macro mineral elements of calcium, chlorine, magnesium, manganese, phosphorous, potassium, silicon, and sodium; and, will preferably contain at least sixty micro mineral elements at concentrations ranging from 0.00001-3.0% by weight percent, from 0.0001-1%, from 0.001% to 1%, from 0.01% to 3%, from 0.1% to 3.0%, by weight percent. The micro mineral elements include aluminum, antimony, arsenic, barium, beryllium, bismuth, boron, bromine, cadmium, cerium, cesium, chromium, cobalt, copper, dysprosium, erbium, europium, fluorine, gadolinium, gold, hafnium, holmium, iodine, indium, iridium, iron, lanthanum, lead, lithium, lutetium, mercury, molybdenum, neodymium, nickel, niobium, palladium, platinum, praseodymium, rhenium, rhodium, rubidium, ruthenium, samarium, scandium, selenium, silver, strontium, sulfur, tantalum, terbium, tellurium, thallium, thorium, thulium, tin, titanium, tungsten, vanadium, ytterbium, yttrium, zinc, and zirconium.

The extraction process used to make an extracted mineral element composition s of the present disclosure normally does not introduce any minerals as part of the extraction process. Therefore, the source materials, the original clay or other soil that is processed through the extraction method, likely include aluminum silicates and other metal silicates in nature that have been naturally enriched with multiple detectable minerals. If a mineral element is identified and quantified in the aqueous liquid extract, generally, it will be identified and quantified in the dry powdered extract in much higher concentrations as a result of drying process or volume reduction.

For example, an extract composition, liquid and dry forms, produced using the soil and extractions methods described in U.S. Pat. No. 8,709,497, incorporated herein by reference, was tested by an independent analytical laboratory, Teledyne Wah Chang Laboratories in Huntsville, Ala., utilizing scientifically accepted and standard equipment such as titration, inductively coupled plasma mass spectrometry, and atomic absorption equipment. The results in the mineral element quantification data are set forth below in TABLE I for an aqueous an extracted mineral element composition and from the dry an extracted mineral element composition that resulted when the aqueous an extracted mineral element composition was dried to produce a powder.

TABLE I

| Mineral Extract Composition | | |
|---|---|---|
| Element | Concentration in aqueous liquid composition | Concentration in dry powder |
| Macro Mineral Elements | | |
| Calcium | 2900 ppm | 8% |
| Chlorine | 170 mg/ml | 0.84%* |
| Magnesium | 460 ppm | 0.95% |
| Manganese | 8.6 ppm | 240 ppm |
| Phosphorous | 0.2 g/L | 0.43% |
| Potassium | 220 mg/L | 1.2% |
| Silicon | 130 mg/L | 0.36% |
| Sodium | 720 mg/L | 2.0% |
| Micro Minerals Elements | | |
| Aluminum | 540 ppm | 0.65% |
| Antimony | 460 ppb | 16.0 ppm |
| Arsenic | 11 ppm | 3.1 ppm |
| Barium | 340 ppb | 11.0 ppm |
| Beryllium | 0.29 ppm | 0.01 ppm |
| Bismuth | <50 ppb | <1.0 ppm |
| Boron | 2.0 mg/L | 72. ppm |
| Bromine | * Present as part of Chlorine assay | |
| Cadmium | <50 ppb | 1.10 ppm |
| Total Organic Carbon | 12/L | Trace |
| Cerium | 1600 ppb | 68.00 ppm |
| Cesium | 82 ppb | 2.00 ppm |
| Chromium | 1.8 ppm | 5.00 ppm |
| Cobalt | 0.25 ppm | 1.00 ppm |
| Copper | 0.09 ppm | <1.00 ppm |
| Dysprosium | 230 ppb | 9.00 ppm |
| Erbium | 150 ppb | 6.00 ppm |
| Europium | <50 ppb | 2.00 ppm |
| Fluorine | * Present as part of Chlorine assay | |
| Gadolinium | 220 ppb | 9.00 ppm |
| Gallium | 70 ppb | 2.40 ppm |
| Germanium | <50 ppb | <1.00 ppm |
| Gold | <50 ppb | <1.00 ppm |
| Hafnium | <0.5 mg/L | 5.00 ppm |
| Holmium | <50 ppb | 2.00 ppm |
| Iodine | * Present as part of Chlorine assay | |
| Indium | <50 ppb | Trace |
| Iridium | <50 ppb | <1.00 ppm |
| Iron | 730 ppm | 28.00 ppm |
| Lanthanum | 650 ppb | 28.00 ppm |
| Lead | <50 ppb | <1.00 ppm |
| Lithium | 0.9 mg/L | <1.00 ppm |
| Lutetium | <50 ppb | <1.00 ppm |
| Mercury | Trace | <1.00 ppm |
| Molybdenum | 3200 ppb | 120.00 ppm |
| Neodymium | 1000 ppb | 45.00 ppm |
| Nickel | 0.74 ppm | 2.00 ppm |
| Niobium | 96 ppb | 3.00 ppm |
| Palladium | <500 ppb | <1.00 ppm |
| Platinum | <50 ppb | <1.00 ppm |
| Praseodymium | 290 ppb | 10.00 ppm |
| Rhenium | <50 ppb | <1.00 ppm |
| Rhodium | <50 ppb | <1.00 ppm |
| Rubidium | 360 ppb | 11.00 ppm |
| Ruthenium | <50 ppb | <1.00 ppm |
| Samarium | 250 ppb | 10.00 ppm |
| Scandium | <400 ppb | 4.00 ppm |
| Selenium | 0.63 mg/L | 21.00 ppm |
| Silver | <0.02 ppm | <5.00 ppm |
| Strontium | 14000 ppb | 420.00 ppm |
| Sulfur | 1.1 g/L | 1.8% |
| Tantalum | <50 ppb | <1.00 ppm |
| Terbium | <50 ppb | 2.00 ppm |

TABLE I-continued

| Mineral Extract Composition | | |
|---|---|---|
| Element | Concentration in aqueous liquid composition | Concentration in dry powder |
| Tellurium | <50 ppb | <1.00 ppm |
| Thallium | <50 ppb | 1.00 ppm |
| Thorium | 640 ppm | 22.00 ppm |
| Thulium | <50 ppb | 1.00 ppm |
| Tin | <50 ppb | <1.00 ppm |
| Titanium | 9.34 ppm | 210.00 ppm |
| Tungsten | 52 ppb | 17.00 ppm |
| Vanadium | 4.3 ppm | 14.00 ppm |
| Ytterbium | 140 ppb | 6.00 ppm |
| Yttrium | 1300 ppb | 61.00 ppm |
| Zinc | 1.2 ppm | 14.00 ppm |
| Zirconium | 2.0 mg/L | 62.00 ppm |

The extracted mineral element composition set forth above in Table I was produced from naturally occurring soil the analysis of which is reflected below in Table II.

TABLE II

| Analysis of Naturally Occurring Soil Macro Mineral Elements | |
|---|---|
| Element | Concentration in ppm by weight unless noted as % Element (for weight percent) |
| Silicon | 25.0% |
| Aluminum | 9.3% |
| Potassium | 4.8% |
| Magnesium | 0.83% |
| Sulfur | 1.6% |
| Iron | 1.6% |
| Calcium | 4.1% |
| Titanium | 0.23% |
| Sodium | 0.138% |
| Manganese | 150 |
| Gallium | 25 |
| Molybdenum | 61 |
| Germanium | 25 |
| Iodine | 7 |
| Bromine | 5.2 |
| Tungsten | 8.1 |
| Hafnium | 2.0 |
| Tantalum | 0.50 |
| Zirconium | 10 |
| Arsenic | 0.2 |
| Antimony | 29 |
| Selenium | 4.1 |
| Zinc | 20 |
| Samarium | 3.5 |
| Holmium | 1.1 |
| Terbium | 0.62 |
| Iridium | 0.51 |
| Lutetium | 0.45 |
| Chromium | 70 |
| Lanthanum | 18 |
| Ruthenium | 7.8 |
| Yttrium | 1.2 |
| Indium | 0.38 |
| Lead | <17 |
| Niobium | 2.89 |
| Carbon | 0.19 |
| Hydrogen | 0.05 |
| Nitrogen | 0.03 |
| Scandium | 3.7 |
| Cobalt | 4.8 |
| Ytterbium | 1.4 |
| Strontium | 240 |
| Barium | 390 |
| Gold | 0.68 |
| Europium | 0.49 |
| Neodymium | 20 |
| Cerium | 40 |
| Cesium | 183 |
| Thorium | >100 |
| Uranium | >100 |
| Nickel | 60 |
| Beryllium | 0.10 |
| Bismuth | 14.3 |
| Boron | 7 |
| Cadmium | 1.12 |
| Chloride | 6100 |
| Copper | 2.2 |
| Fluoride | 3.85 |
| Lithium | 1.44 |
| Mercury | 0.166 |
| Palladium | 0.74 |
| Phosphate | 320 |
| Platinum | 0.08 |
| Rhodium | 0.44 |
| Rubidium | 36.5 |
| Silver | 0.3 |
| Tellurium | 0.1 |
| Thulium | 0.65 |
| Tin | 0.44 |
| Vanadium | 8 |
| Dysprosium | 4.0 |
| Praseodymium | 2.0 |
| Thallium | 10 |
| Rhenium | 1.0 |
| Erbium | 2.0 |
| Oxygen | 0.2 |

Once a desirable naturally occurring soil or soil combination is obtained, the soil or soil combination is subjected to the extraction process described by U.S. Pat. No. 8,709,497. Clay soils, mixtures of clay soils, or mixtures of clay soil(s) and leonardite are preferred in the practice of the disclosure. One reason such soil combinations are preferred is that such soils can be high in the mineral elements deemed important in the practice of the disclosure. In an aspect, an extracted mineral element composition, produced in accordance with the disclosure, comprises at least eight macro mineral elements and at least sixty micro mineral elements. In an aspect, an extracted mineral element composition, produced in accordance with the disclosure, may consist essentially of at least eight macro mineral elements and at least sixty micro mineral elements.

The first step in determining whether a clay soil is acceptable as a source material is to determine if arsenic, lead, mercury, and cadmium are each present in acceptably small concentrations. An aspect of the present disclosure comprises compositions having the concentration of each of these elements in lower amounts than the concentrations shown below in Table III.

TABLE III

| Maximum Desired Concentrations of Toxic Elements | |
|---|---|
| Element | Maximum Desired Soil Concentration |
| Arsenic | 0.2 ppm |
| Lead | 0.17 ppb |
| Mercury | 0.116 ppm |
| Cadmium | 1.12 ppm |

TABLE IV

| Preferred Minimum Concentrations of Selected Rare Earth Elements in Naturally Occurring Soil | |
|---|---|
| Element | Preferred Minimum Soil Concentration Element in ppm |
| Cerium | 40 |
| Praseodymium | 2 |
| Neodymium | 20 |
| Samarium | 3.5 |
| Europium | 0.49 |
| Terbium | 0.62 |
| Dysprosium | 4 |
| Holmium | 1 |
| Erbium | 2 |
| Thulium | 0.65 |
| Ytterbium | 1.2 |
| Lutetium | 0.45 |

The concentration of the elements listed in Table IV can vary as desired, but, as noted, it is desirable to have at least the concentration of each element as noted in Table IV. Source material soil for composition of the present disclosure may or may not comprise one or all of the rare earth elements listed in Table IV. For example, a lanthanum concentration of at least eighteen ppm and a scandium concentration of at least three and seven-tenths ppm may be found in a source material soil. Concentrations of promethium and gadolinium may also be found. Source material soil for composition of the present disclosure may or may not comprise at least ten rare earth elements, at least twelve, or more rare earth elements and optionally include lanthanum and scandium. The presence of rare earth elements in the soil, and in an extracted mineral element composition derived from the source material soil, may be useful in improving the efficacy of an extracted mineral element composition when ingested or when applied on the skin for intradermal or transdermal penetration, or for cosmetic or other purposes.

Once a clay soil or clay and soil combination is provided or is combined to yield the mineral elements, as taught by U.S. Pat. No. 8,709,497, the source material soil is subjected to the extraction process as taught by U.S. Pat. No. 8,709,497, to yield an extracted mineral element composition comprised in the compositions of the present disclosure.

In general, the extraction of the source material soil uses the following steps. Water, typically purified using known methods such as reverse osmosis, is added to citric acid and the source material soil in a mixing tank. The amount of citric acid (or of phosphoric acid or other edible acid(s)) or combinations thereof, may be in the range of 0.25% to 7.5% of the weight of water utilized, but typically is in the range of 1.0% to 2.0%. The water, citric acid and source material soil, form a slurry and is gently agitated (for example, with a blade slowly rotating at from one to ten RPM) for about an hour, although the agitation time can vary as desired. The slurry from the tank is directed into a settling tank to permit particulates to settle downwardly out of the slurry. The slurry is maintained in the settling tank for any desired length of time, in the range of about one to ten days. As the length of time that the slurry is maintained in the settling tank increases, the amount of liquid that can be drawn out of the tank and sent to a cooling tank or concentrator increases and the amount of solids that have settled to the bottom of the tank increases. Additives can be used to facilitate the settling of solids from slurry. After the slurry has resided in settling tank for the desired period of time, liquid is drawn out of the tank to a cooling tank, or directly to the concentrator. The solids on the bottom of tank can be reprocessed, discarded, or can be otherwise utilized.

The cooling tank cools the fluid from the settling tank to a temperature in the range of 40-70° F. (5 to 21° C.). Cooled liquid is sent to the concentrator.

The concentrator removes water from the cooled liquid. This may be accomplished using known methods such as a thin film composite reverse osmosis system or evaporation. The resulting concentrate liquid, comprising the minerals extracted from the original slurry, is directed to a cooling tank or to a dryer, depending if storage or further processing is desired. The cooling tank cools the concentrate liquid to 40 to 70° F. (5 to 20° C.) to prevent the growth and yeast and mold.

The concentrate liquid produced by concentrator has a pH of approximately 3. The concentrate liquid typically includes from three to twelve percent by weight mineral elements, i.e. if the mineral elements are separated from the concentrate liquid, a dry material is produced that has a weight equaling about 3% to 12% by weight of the concentrate liquid. The pH of the concentrate liquid is adjusted by varying the amount of citric acid or other edible acid and/or alkaline or acidic soil added to the mixing tank and is in the range of pH 2.0 to pH 5.0, preferably pH 2.5 to pH 3.5. The pH of the concentrate liquid (and dry powder or other material produced therefrom) preferably is less than pH 4.5. An extracted mineral element concentration of at least eight percent may be provided for injection into a dryer. Any desired drying system can be utilized, such as a tower into which the concentrate liquid is sprayed to produce a powder. An extracted mineral element composition includes a liquid extracted mineral element composition, including the concentrate liquid disclosed above, and a dry extracted mineral element composition, as disclosed above. One of skill in the art would know which form of an extracted mineral element composition is to be used in compositions comprising an extracted mineral element composition.

Minerals are involved in the body in a vast array of complex reactions, most of which are dependent on mineral chemical characteristics. Minerals, such as those in the form of electrolytes, which maintain fluid and acid-base balance and are chemically active as cofactors in countless enzyme-catalyzed reactions.

An extracted mineral element composition may comprise dry powders, liquid formulations, food compositions, topical compositions and compositions administered by injection or other routes of administration to subjects, including humans and animals. Other components may be added to an extracted mineral element composition or an extracted mineral element composition may be added to a second composition to form a composition comprising an extracted mineral element composition which may be used in methods disclosed herein to provide muscle loss and/or bone loss modulating activity.

A composition of the present disclosure may comprise an extracted mineral element composition and vitamins and/or amino acids, including but not limited to whey protein or casein, amino acids (such as leucine, branched amino acids and hydroxymethylbutyrate), triglycerides, Vitamins A, B6, B12, folate, C, D, K, vitamin D analogues and E, carnitine, lipoic acid, creatinine, and coenzyme Q. A composition of the present disclosure may comprise an extracted mineral element composition β-hydroxy-β-methylbutyrate (HIVIB). In some embodiments, a composition of the present disclosure may comprise ghrelin receptor ligand or growth hormone analogues and secretagogues, such as, pralmorelin, examorelin, tabimorelin, capimorelin, capromorelin, ipamorelin, EP-01572, EP-1572, JMV-1843, an androgenic/anabolic steroid such as testosterone/oxandrolone; a melanocortin 4 receptor agonist, such as bremelanotide, a ghrelin or analogue thereof, such as human ghrelin, CYT-009-GhrQb, L-692429, GHRP-6, SK&F-110679, U-75799E), leptin (metreleptin, pegylated leptin; a leptin receptor agonist, such as LEP(116-130), OB3, [D-Leu4]-0B3, rAAV-leptin, AAV-hOB, rAAVhOB; an insulin (short-, intermediate-, and long acting formulations); a cortisol or corticosteroid, or combinations thereof. Such compositions may be used, in methods disclosed herein, for example, in treating sarcopenia or a musculoskeletal condition. In an embodiment, a composition may comprise an agent which treats bone diseases, disorders or conditions, such as osteoporosis, bone fractures, or markers to monitor bone activity.

A composition of the present disclosure may comprise an extracted mineral element composition and growth promoting agents such as but not limited to TRH, diethylstilbesterol, theophylline, enkephalins, E series prostaglandins growth hormone secretagogues such as GHRP-6, GHRP-1, GHRP-2, growth hormone releasing factor and its analogs or growth hormone and its analogs, or with alpha-adrenergic agonists, such as clonidine or serotinin 5-HTD agonists, such as sumatriptan, or agents which inhibit somatostatin or its release, such as physostigmine and pyridostigmine, parathyroid hormone, PTH(1-34) or bisphosphonates, such as MK-217 (alendronate estrogen, a selective estrogen receptor modulator, such as tamoxifene or raloxifene, or other androgen receptor modulators, progesterone receptor agonists ("PRA"), such as levonorgestrel, medroxyprogesterone acetate (MPA), antiresorptive agents, elemental calcium and calcium supplements, cathepsin K inhibitors, MMP inhibitors, vitronectin receptor antagonists, Src SH2 antagonists, vacular-H.sup.+-ATPase inhibitors, ipriflavone, fluoride, tibolone, prostanoids, 17-β hydroxysteroid dehydrogenase inhibitors or Src kinase inhibitors.

A composition of the present disclosure may comprise an extracted mineral element composition and bone stimulating agents such as but not limited to bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-C SF, a chemokine, such as eotaxin, a collagen, osteocalcin, osteonectin or others known to those skilled in the art.

A composition of the present disclosure may comprise an extracted mineral element composition formulated to be a medicament, a food product, nutritional supplement and/or nutraceutical composition. A nutrition composition may further comprise a protein source, a fat source and/or a carbohydrate source. A composition may comprise an extracted mineral element composition in a nutritionally balanced foodstuff, a nutritionally complete formula, a dietary supplement, a dairy product, a chilled or shelf stable beverage, a soup, a nutritional bar, pet food, animal feed, a confectionery, a pharmaceutical composition or combinations thereof. Compositions comprising an extracted mineral element composition may include but not limited to, water, which may be still or carbonated, and other ready to drink or ready to mix beverages, including but not limited to coffees, teas, energy drinks, juices, milks, and plant liquids such as soy products, sugar cane products, coconut products, protein drinks, meal replacement drinks, varieties of ENSURE® or Boost or other known nutritional supplement drinks or foods, and alcohol containing products such as liquors, ciders, beer and wine. Composition for muscle and/or bone loss modulating compositions may comprise pharmaceutical, nutraceutical or dietary supplement compositions in combination with an extracted mineral element composition. For example, a muscle and/or bone loss modulating composition may comprise liquid pharmaceutically acceptable syrups, excipients, fillers or other known pharmaceutical formulations in combination with an extracted mineral element composition.

Solid or dry muscle and/or bone loss modulating compositions may comprise an extracted mineral element composition and include, but are not limited to, foodstuffs, food products, nutritive and non-nutritive sweeteners, pharmaceutical, nutraceutical or dietary supplement formulations. For example, a muscle and/or bone loss modulating composition may comprise solid or dry pharmaceutically acceptable compositions, excipients, fillers or other known pharmaceutical formulations, to be made into dosage units such as tablets, capsules or powders, in combination with a an extracted mineral element composition. The compositions of the present disclosure may function as additives to foods, and be combined with food products, including foods wherein a dry or liquid extracted mineral element composition can be added, so as to provide muscle and/or bone loss modulating activity to the food or drink. Muscle regenerative compositions may also be administered topically. Topical compositions may have anti-aging and cosmetic effects. Loss of muscle mass and tone are a part of aging and such aging is often apparent in the facial muscles.

An effective amount of an extracted mineral element composition may or may not be dependent on whether the compositions of the present disclosure are added to other compositions, for example, to a foodstuff. A muscle and/or bone loss modulating composition comprising an extracted mineral element composition may be provided or administered to a subject 1 time a day, two times a day, three times a day or more often. A muscle and/or bone loss modulating composition comprising an extracted mineral element composition may be administered daily, weekly, or monthly in a regular schedule or on an as needed schedule. In general, a muscle and/or bone loss modulating composition may comprise from about 0.0001 g to about 1000 g of the extracted mineral element composition, or from about 0.0001 g to about 100 g, from about 0.0001 g to about 10 g, from about 0.001 g to about 1000 g, from about 0.01 g to about 1000 g, from about 0.1 g to about 1000 g, from about 1.0 g to about 100 g, from about 1.0 g to about 10 g, from about 10 g to about 1000 g, and ranges therein between. For example, a 12 oz enhanced water beverage may contain 0.1 gram of an extracted mineral element composition, while a 10 oz carbonated beverage with high fructose corn syrup may contain 10 grams of an extracted mineral element composition, and a gallon size maple syrup may contain 300 grams of a an extracted mineral element composition.

Compositions disclosed herein are used in methods of the present disclosure. Methods of the present disclosure include methods of inhibiting or reducing muscle degeneration, diseases and conditions which cause a decrease in muscle mass, muscle atrophy, inactivity atrophy, Dejerine Sottas syndrome (HSMN Type III), extended bedrest, cachexia, co-morbidities with cancer, congestive heart failure (CHF), chronic obstructive pulmonary disease (COPD), burns, liver failure, liver disease, starvation, muscle degeneration, sarcopenia, lack of exercise, post-space travel conditions, aids in treatment of structural defects in the muscle (muscular dystrophy), or by inflammatory reactions in the body directed against muscle (the myopathies); osteoporosis, osteopenia, increased bone resorption, bone fracture, bone frailty, loss of bone mineral density (BMD), facial aging, or any combination thereof. Methods for inhibiting or reducing muscle mass loss and bone mass loss, prevention, reduction, or treatment of muscle mass loss-related conditions and bone mass loss-related conditions comprise administering or providing an effective amount of a muscle and/or bone loss modulating composition comprising an extracted mineral element composition to a human or animal, wherein the muscle and/or bone loss modulating composition alters muscle and/or bone loss in the subject.

Methods of the present disclosure comprise making and using muscle and/or bone loss modulating compositions. Such compositions may be consumed by healthy young and adult animals and humans, as well as humans or animals at risk for developing, or suffering from, muscle and/or bone loss-related conditions. Food, beverages, and nutritional supplement compositions and other treatments may be provided to a subject before, concurrently or after providing the compositions taught herein.

Compositions comprising a muscle and/or bone loss modulating composition, may comprise herbals or extracts of herbals such as Siraitia grosvenorii (luo han guo), ginger, Chinese thunder god vine, willow bark extract, feverfew, cat's claw, stinging nettle, boswellia, S-adenosylmethionine (SAMe), chondroitin sulfate, glucosamine, mogrosides, essential fatty acids, and enzymes, such as bromelain, and quercetin.

Muscle and/or bone loss modulating compositions for these and other muscle degeneration-related conditions may comprise ready-to-eat-cereals, fruit juices, candy bars, chewing gum, nutritional supplements, enhanced water beverages, carbonated and non-carbonated drinks, alcoholic beverages such as liquors, ciders, beer and wine, baby food, and many other foodstuffs and beverages. The muscle and/or bone loss modulating compositions of the present disclosure may be used an animal feed additive.

Definitions Used Herein

Chemical element. Any of more than 100 fundamental metallic and nonmetallic substances that consist of atoms of only one kind and that either singly or in combination constitute all matter, most of these substances lighter in weight than and including uranium being found in nature and the rest being produced artificially by causing changes in the atom nucleus.

Clay. A natural or synthetic colloidal lusterless earthy composition that includes tiny sheet-like layered particles of alumina and/or silica that are less than about 0.002 millimeters in size, that is generally plastic when moist, and that, when naturally occurring, includes decomposed igneous and/or metamorphic rocks. Most clays have a pH in the range of about 4.5 to 8.5. Natural and synthetic clays include mineral elements. Clays can, in additional to having particles less than five microns in size, include particles having a size greater than five microns.

Leonardite. A soft, loose-textured coal that has low BTU value. Leonardite is a humate, can include up to 70% by weight minerals, can be formed from lignite, can occur naturally as the result of not being heated and pressurized over time to the extent necessary to produce anthracite, lignite, or bituminous coal, and, can include compost as a component.

Mineral. Any naturally occurring chemical element or compound. A mineral may have a characteristic crystal structure and chemical composition or range of compositions.

Mineral element. A chemical element that occurs naturally as or in a mineral. A mineral element may be produced using synthetic or manufacturing processes, however, each mineral element does occur naturally as or in a mineral.

Rare earth or rare earth element. Any one of a group of metallic elements with atomic numbers 58 through 71, including cerium, praseodymium, neodymium, promethium, samarium, euroOpium, gadolinium, terbium, dysprosium, holmium, erbium, thulium, ytterbium, and lutetium. In nature, rare earth elements are bound in combination with nonmetallic elements in the form of phosphates, carbonates, fluorides, silicates, and tantalates.

Sand. A loose material consisting of small but easily distinguishable grains usually less than two millimeters in diameter and more than about 0.02 millimeters in diameter, most commonly of quartz, resulting from the disintegration of rocks.

Silt. Unconsolidated or loose sedimentary material whose constituent rock particles are finer than grains of sand and larger than clay particles, specifically, material consisting of mineral soil particles ranging in diameter from about 0.02 to 0.002 millimeters.

It must be noted that, as used in this specification and the appended claims, the singular forms "a," "an," and "the" include plural referents unless the context clearly dictates otherwise. In the context of this application, the wording "a", "an" and "the" imply both the singular as the plural of the noun to which it refers. Hence, the wording "a protein" means one or more proteins.

In the context of this application, the term "or" is defined as "and/or" unless specified otherwise. Hence, the wording "A or B" comprises the individual members A and B, as well as the combined members A and B.

All patents, patent applications and references included herein are specifically incorporated by reference in their entireties.

The terms "treating" and "treatment" as used herein, unless otherwise specified, includes preventing a condition, delaying the onset of a condition, reducing the severity of symptoms of a condition, or eliminating some or all of the symptoms of a condition.

The term "ameliorate" as used herein, unless otherwise specified, means to eliminate, delay, or reduce the prevalence or severity of symptoms associated with a condition.

The term "condition" as used herein, unless otherwise specified, includes pathological and non-pathological conditions, all of which are characterized by an aberration or imbalance in the muscle and/or bone loss of a human or animal, or unfavorable alteration of muscle tone.

The term "modulate" as used herein, unless otherwise specified, means to increase muscle or bone mass or to reduce the muscle and/or bone mass loss in the body, or to increase or decrease muscle tone to reach a desirable physiological range.

All percentages, parts and ratios as used herein are by weight of the total composition, unless otherwise specified. All such weights as they pertain to listed ingredients are based on the amount of extract used, and, therefore, do not include solvents or by-products that may be included in commercially available materials, unless otherwise specified.

All numerical ranges as used herein, whether or not expressly preceded by the term "about", are intended and understood to be preceded by that term, unless otherwise specified.

All references to singular characteristics or limitations of the present disclosure shall include the corresponding plural characteristic or limitation, and vice versa, unless otherwise specified or dearly implied to the contrary by the context in which the reference is made.

All combinations of method or process steps as used herein can be performed in any order, unless otherwise specified or dearly implied to the contrary by the context in which the referenced combination is made.

The methods of the present disclosure may also be substantially free of any optional or selected essential feature described herein, provided that the remaining method still contains all of the required limitations as described herein.

As used herein, the term "administering" refers to bringing a subject in contact with a compound of the present disclosure. As used herein, administration can be accomplished in vitro, i.e. in a test tube, or in vivo, i.e. in cells or tissues of living organisms, for example humans. In one embodiment, the present disclosure encompasses administering the compounds of the present disclosure to a subject.

The compositions disclosed herein can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the composition can be delivered to tissue (e.g., needle or catheter). Alternatively, topical administration may be desired for application to mucosal cells, for skin or ocular application. Another method of administration is via aspiration or aerosol formulation.

It is to be understood that any of the above means, timings, routes, or combinations thereof, of administration of two or more agents is to be considered as being encompassed by the phrase "administered in combination", as described herein.

Compositions disclosed herein may be administered to humans and/or animals, of any sex or age, including in utero. Animals includes those animals kept as pets, wild animals or farm-raised animals, including but not limited to, and are generally applicable to any farmed food animal such as, without limitation, swine (domestic pig, wild boars), bovine (bison, cattle, yaks), cervids (deer, elk, moose), ovine (sheep/lamb), caprine (goats), lagomorphs (rabbit, pika), avian (chicken, turkey, duck, game birds, emu/ostrich), fish (catfish, tilapia, salmon, red drum), shellfish (crustaceans such as crab, lobster, shrimp; and mollusks such as clams, octopus, squid), roe (caviar), amphibians (frogs, salamanders), reptiles (snakes, turtle, alligator), canids (dog, fox), felines (cat), equines (horse, donkey, zebras), marsupials (kangaroo, opossum), insects (grasshopper, beetles, larvae), primates (gorilla, monkey), rodents (rat, mouse, squirrel, beaver), cetaceans (whale, dolphin), pinnipeds (walrus, seal), and miscellaneous (bear, raccoon, elephant, llamas and alpacas).

It should be understood, of course, that the foregoing relates only to preferred embodiments of the present disclosure and that numerous modifications or alterations may be made therein without departing from the spirit and the scope of the disclosure as set forth in this disclosure.

The present disclosure is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

EXAMPLES

Example 1

Materials & Methods

Test Materials

RFA2107-61 (Totala Liquid 101 which is the liquid concentrate extracted mineral element composition). RFA2107-64 (ENSURE®), RFA2107-64B (ENSURE®+ 200 mg Totala Dry) and RFA2107-64D (Totala Dry). Totala Dry (the dry extracted mineral element composition) was dissolved at 200 mg/ml (100%) and was further diluted, along with other test materials to 4% (dilution factor 1/25, v:v). All test materials were stored at room temperature, were diluted in type I sterile water the day of the experiment and were tested at 0.2% (v:v, final concentration).

Cells

Human skeletal muscle cells (HSMC p.3 myoblasts/satellite cells, Cell Applications, cat. #150K-05a) were plated in cell type-specific Cell Applications growth media and were exposed to 0.2% test materials for 24 h. Cells were then exposed to 300 μM hydrogen peroxide ($H_2O_2$) treatment for 4 h, afterward the culture was stopped by placing cells in RNAlater solution at 4° C.

Gene Expression Quantification

Cells were lysed and total RNA was extracted and purified with Illustra mini RNAspin kit (GE Healthcare, cat. #95017-489). Furthermore, a second DNase treatment (using Turbo DNAase from Ambion cat. #BP1907) was added at the end of the procedure to guarantee the quality of the genomic DNA-free total RNA. The purity and quantity of each RNA preparation was validated by measuring absorbance at 260 nm and 280 nm with Agilent HP-8452A diode array spectrophotometer. The expression of genes of interest was measured by real-time quantitative PCR with BioRad iCycler iQ Detection System using primers reported in Table I, with 1st strand synthesis kit, SYBR Green master mix and PCR running conditions from Qiagen (formerly SA Biosciences). Efficiency ΔΔCt was used for quantification of results, using the expression of GAPDH housekeeping control gene (primers: F: GAGTCAACGGATTTGGTC; SEQ ID NO: 1; R: CAACAATATCCACTTTACCAGAG, SEQ ID NO: 2) as the reference gene. Genes were considered differentially expressed if fold up- or downregulation was 2 or more. Differences with p values not greater than 0.05 (as determined by paired Student test) were considered statistically significant.

TABLE V

| Sequences of primers used in this project. | | | |
|---|---|---|---|
| Oligo Name | Direction | Sequence 5' to 3' | SEQ ID NO: |
| MHCIIa | FORWARD | CAATCTAGCTAAATTCCGCAAGC | 3 |
| CCL5 | FORWARD | CCCATATTCCTCGGACAC | 4 |
| mTOR | FORWARD | TCGTGCCTGTCTGATTCTC | 5 |
| SOD1 | FORWARD | GAGCAGAAGGAAAGTAATGG | 6 |
| HMOX1 | FORWARD | GGCCTGGCCTTCTTCACCTT | 7 |
| hTERT | FORWARD | GCGGAAGACAGTGGTGAACT | 8 |
| IFG-1 | FORWARD | TTTCAACAAGCCCACAGGGT | 9 |
| myostatin | FORWARD | CCGTCGAGACTCCTACAAC | 10 |
| BCL2 | FORWARD | TTCTTTGAGTTCGGTGGGGTC | 11 |
| ATP5D | FORWARD | TTGTGAGCAGCGGTTCCA | 12 |
| MHCIIa | REVERSE | TCACTTATGACTTTTGTGTGA | 13 |
| CCL5 | REVERSE | TGGTGTAGAAATACTCCTTGA | 14 |
| mTOR | REVERSE | GATTCATGCCCTTCTCTTTGG | 15 |
| SOD1 | REVERSE | TACACCACAAGCCAAACGAC | 16 |
| HMOX1 | REVERSE | GAGGGGCTCTGGTCCTTGGT | 17 |
| hTERT | REVERSE | AGCTGGAGTAGTCGCTCTGC | 18 |
| IFG-1 | REVERSE | GGAGTCTGTCCGTAGCACC | 19 |
| myostatin | REVERSE | ACACTGTCTTCACATCAATGC | 20 |
| BCL2 | REVERSE | TGCATATTTGTTTGGGGCAGG | 21 |
| ATP5D | REVERSE | CCAACAACTGCACCGAAGAGT | 22 |

Results and Discussion

Effect of $H_2O_2$ Treatment on Human Muscle Cells.

Reactive oxygen species (ROS) such as hydrogen peroxide ($H_2O_2$) are formed during mitochondrial respiratory processes. If left uncontrolled, they can produce a large variety of DNA damage and induce premature senescence. This is particularly true in muscle cells, whose mitochondrial metabolism is geared to produce high levels of energy, and thus high levels of ROS. Here, we aimed at reproducing such high ROS conditions in vitro by incubating muscle cells with high (but not cytotoxic) concentrations of $H_2O_2$.

$H_2O_2$ oxidizes the redox potential of muscle cells, prompting accelerated senescence, where the muscle formation (myogenesis) and regenerative potential are greatly decreased (Hansen et al., 2007).

Challenging human muscle cells with $H_2O_2$ for 4 h expectantly did not result in macroscopic changes in cellular morphology, which would indicate acute cytotoxicity. The deleterious effect of $H_2O_2$ could be nevertheless appreciated by the decreased amount of mitotic cells, as observed through the inverted cell culture microscope with .times.40 magnification).

At the molecular level, $H_2O_2$ treatment resulted in oxidative stress, to which cells predictably responded by increasing the expression of heme oxygenase 1 (HMOX1) gene. HMOX1 protein product is a stress inducible enzyme acting as cytoprotectant against reactive oxygen species, such as hydrogen peroxide, and its increase of expression demonstrates that our experimental system successfully functioned as reported in the literature (Nose et al., 1991; Willis et al., 1996).

Another gene, whose expression has been upregulated by the $H_2O_2$ shock was the anti-oxidant, antiapoptotic BCL-2. This upregulation, especially important in muscle cells due to the BCL-2 role in protecting calcium homeostasis, is also in agreement with published literature (Distelhorst etal., 1996; Tu et al., 1996; Bruce-Keller et al., 1998).

Interestingly, MHCIIa (myosin heavy chain form IIa) was also affected by the hydrogen peroxide treatment. The decrease of expression of MHCIIa—a key marker of muscle senescence (Balagopal et al., 2001)—constitutes a new, unpublished finding and is consistent with the $H_2O_2$ model of accelerated aging and muscle degeneration.

In summary, the observed increase of expression of HMOX1 and BCL2 in response to $H_2O_2$ shock is consistent with their role of protecting cells from damage and death. The products of these genes act by eliminating free radicals, and stimulating regenerative/reparative mechanisms, which restore the cellular homeostasis. Furthermore, the observed decrease of MHCIIa is consistent with the accelerated senescence effect caused by exposure of muscle cells to sub-cytotoxic concentrations of hydrogen peroxide.

TABLE VI

| Genes modulated by $H_2O_2$ treatment of human muscle cells. | | | |
|---|---|---|---|
| Fold | Gene Symbol | Gene Product Name | Function |
| 3.7 | BCL-2 | B-cell CLL/lymphoma 2 | Anti-apoptotic, anti-oxidant |
| 4.3 | HMOX1 | Heme oxygenase 1 | Anti-oxidant |
| −4.0 | MYH2 | MHCIIa, Myosin heavy chain IIa | Responsible for muscle mass and contraction, MHCIIa dramatically decreases with age |

Effect of 0.2% ENSURE® (Abbott Nutrition) on $H_2O_2$-Treated Human Muscle Cells.

ENSURE® potentiated the anti-oxidant response in $H_2O_2$-treated cells by further enhancing the expression of HMOX1 and by stimulating SOD1 (superoxide dismutase 1)—enzymes involved in free radical scavenging. It also increased the expression of NFKB 1—a redox-sensitive transcription factor, generally regarded as pro-inflammatory. Its activation occurs at the posttranscriptional level and the significance of its expressional activation is unclear. One hypothesis is that ENSURE® inhibits its posttranscriptional activation, which triggers a feedback loop resulting in the compensatory raise of its transcription rate. Another hypothesis would be that the induction of NFKB1 being part of the physiological response to oxidative stress, it is facilitated by ENSURE® as a part of the defensive mechanism. Clearly more studies are needed to elucidate the overall effect of ENSURE® on this transcription factor and the signal transduction pathways under its control. However, downstream pro-inflammatory cytokine controlled by this transcription factor—CCL5 was not activated, suggesting that NFKB1 activation by ENSURE® does not translate into a pro-inflammatory response.

TABLE VII

| Genes modulated by 0.2% ENSURE ® in the $H_2O_2$-treated human muscle cells Fold Gene Symbol Gene Product Name Function | | | |
|---|---|---|---|
| Fold | Gene Symbol | Gene Product Name | Function |
| 4.0 | HMOX1 | Heme oxygenase 1 | Anti-oxidant |
| 3.1 | SOD1 | Superoxide dismutase 1 | Anti-oxidant |
| 4.2 | NFKB1 | EBP-1, KBF1, NF- K-B, p105, p50, (Nuclear factor of kappa light polypeptide gene enhancer in B-cells 1) | Pro-inflammatory, induced by free radicals |

Effect of adding 200 mg of Totala Dry to Ensure in the $H_2O_2$-Treated Human Muscle Cell Model.

There was only 1 gene differentially expressed between Ensure and Ensure with 200 mg Totala Dry. However, this gene-coding for myosin heavy chain IIa is an extremely important marker for muscle senescence (its expression decreases by 38% between the age of 20 and 70, Balagopal et al., 2001). Over 3-fold stimulation of the expression of this protein adds a considerable myo-regenerative potential to ENSURE®'s activity profile.

TABLE VIII

| Genes modulated by 0.2% ENSURE ® with 200 mg Totala Dry vs. 0.2% ENSURE ® in the $H_2O_2$-treated human muscle cell model. | | | |
|---|---|---|---|
| Fold | Gene Symbol | Gene Product Name | Function |
| 3.5 | MYH2 | MHCIIa, Myosin heavy chain IIa | Responsible for muscle mass and contraction, MHCIIa dramatically decreases with age |

Effect of Totala Dry (0.2% of Totala Dry 200 mg/ml) on $H_2O_2$-Treated Human Muscle Cells.

Similarly to Ensure, Totala Dry increases the NFKB1 expression (see the ENSURE® paragraph above for details). Totala Dry potentates the anti-oxidant response of muscle cells challenged with $H_2O_2$ by increasing the expression of HMOX1 and BCL-2 (already upregulated by the natural anti-oxidant cellular defenses). The further increase of BCL-2 expression is particularly important, because of its triple role in preventing apoptosis (cell death), neutralizing free radicals and preserving intracellular calcium homeostasis, the latter being a critical factor for proper muscle performance, through the excitation/contraction coupling function (E-C coupling; Distelhorst et al., 1996; Endo, 2006) Furthermore, Totala Dry fully reverses the free radical-induced suppression of MYH2 expression in muscle cells, restoring the pre-senescence production level for this fundamentally important muscle protein. Interestingly, in this respect, Totala Dry has the same effect on muscle myosin as physical exercise (Aguiar et al., 2010). Note that addition of Totala Dry to ENSURE® produced similar stimulatory effect on MYH2.

TABLE IX

| Genes modulated by 0.2% Totala Dry in $H_2O_2$-treated human muscle cells. | | | |
|---|---|---|---|
| Fold | Gene Symbol | Gene Product Name | Function |
| 3.1 | BCL-2 | B-cell CLL/lymphoma 2 | Anti-apoptotic, anti-oxidant |
| 3.8 | HMOX1 | Heme oxygenase 1 | Anti-oxidant |
| 4.6 | MYH2 | MHCIIa, Myosin heavy chain IIa | Responsible for muscle mass and contraction, MHCIIa dramatically decreases with age |
| 2.8 | SOD1 | Superoxide dismutase 1 | Anti-oxidant |
| 3.1 | NFKB1 | EBP-1, KBF1, NF- K-B, p105, p50, (Nuclear factor of kappa light polypeptide gene enhancer in B-cells 1) | Pro-inflammatory, induced by free radicals |

Effect of 0.2% Totala Liquid on $H_2O_2$-Treated Human Muscle Cells.

The gene expression profiles of Totala Dry- and Totala Liquid-treated cells were very similar. Giving the similarity of both test materials, this underlines the high reproducibility of the experimental procedures and adds confidence that the obtained results are true. Furthermore, out of 5 genes, which were found to be upregulated in this project, 2 (HMOX1 and SOD1) were found to be upregulated by Totala Liquid also in human dermal fibroblasts, using the DNA microarray technique (the other 3 genes were found unchanged in fibroblasts). With the Totala Liquid and Totala Dry results being very similar, please refer to the Totala Dry paragraph above for further discussion of Totala Liquid results.

Conclusion

Totala formulations were found to have a unique ability to revert the decrease of the most important structural and functional component of human muscles, with the added capacity to potentiate natural anti-apoptotic and anti-oxidant defenses in human skeletal muscle cells. When added to ENSURE®, Totala stimulated the expression of myosin heavy chain IIa, which is in line with ENSURE®'s claim of "rebuilding muscle and strength naturally lost over time". Such molecular substantiation of ENSURE®'s claim was missing in the ENSURE® sample without Totala.

TABLE X

| Genes modulated by 0.2% Totala Liquid in $H_2O_2$-treated human muscle cells. | | | |
|---|---|---|---|
| Fold | Gene Symbol | Gene Product Name | Function |
| 3.1 | BCL-2 | B-cell CLL/lymphoma 2 | Anti-apoptotic, anti-oxidant |
| 3.8 | HMOX1 | Heme oxygenase 1 | Anti-oxidant |
| 4.6 | MYH2 | MHCIIa, Myosin heavy chain IIa | Responsible for muscle mass and contraction, MHCIIa dramatically decreases with age |
| 2.8 | SOD1 | Superoxide dismutase 1 | Anti-oxidant |
| 3.1 | NFKB1 | EBP-1, KBF1, NF- K-B, p105, p50, (Nuclear factor of kappa light polypeptide gene enhancer in B-cells 1) | Pro-inflammatory, induced by free radicals |

Example 2

Materials. In the studies described herein, the nutritional drink was Isagenix Cleanse (Lot #10330209-293; Isagenix International LLC, Chandler, Ariz., US). The extracted mineral element composition was provided in dry form or in a liquid form. (Mineral Biosciences, LLC, Goodyear, Ariz., US). The cells were adult human skeletal muscle cells ("HSkMC"; Cell Applications, Inc., San Diego, Calif., US) and human osteoblasts ("HOb"; Cell Applications, Inc., San Diego, Calif., US). Cells were cultured in the growth medium recommended by the manufacturer.

Methods. To test the effect of nutritional drink with and without extracted mineral element composition (each referred to as "test article"), cells were exposed to 1% (v/v) of the test article in growth media that was a 1:1 mixture of the cell type specific growth media and DMEM. Cells were exposed to this test article-containing media for 72 hours. At the end of this incubation period, the metabolic activity and total insoluble protein were assessed by a MTT assay and a sulforhodamine B assay, respectively. It is believed that insoluble protein represents the structural proteins in the cells. The MTT and sulforhodamine B assays were carried out as previously described (Berridge, M. V. and Tan, A. S. (1993) Arch. Biochem. Biophys. 303:474-482; Skehan, P., et al. (1990) J. Natl. Cancer Inst. 82:1107-1112, respectively). Differences with p values less than 0.05 (as determined by paired Student test) were considered statistically significant. All values for metabolic activity and protein determined in cells exposed to nutritional drink with extracted mineral element composition were normalized to the response of cells exposed to nutritional drink without extracted mineral element composition (i.e., the 100% response level).

Figure 2:
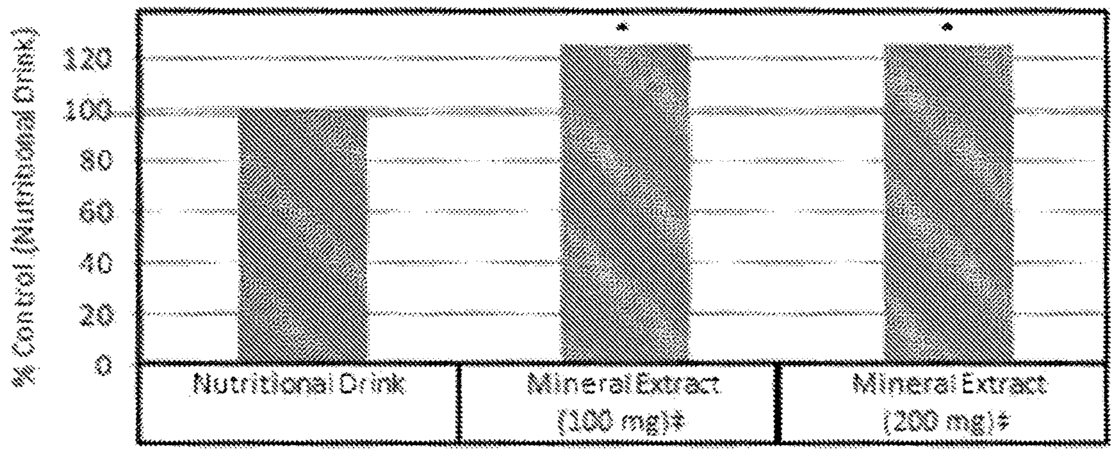
FIG. 2 shows representative data for human osteoblast cells ("HOb") exposed to nutritional drink with the indicated amounts of an extracted mineral element composition compared to nutritional drink without an extracted mineral element composition. The data show the effect on metabolic activity as indicated in the figure. All data are plotted as normalized values compared to the response in cells exposed to nutritional drink without an extracted mineral element composition (i.e., the 100% control level).

Results. The test results are shown in FIGS. 1 and 2. The data in FIG. 1 show that when HSkMC cells were exposed to 1% (v/v) nutritional drink containing an extracted mineral element composition for 72 hr there was a statistically significant increase in metabolic activity as determined using the MTT assay. The relative increase in metabolic activity in HSkMC cells was similar for nutritional drink containing either 100 mg/mL or 300 mg/mL dry powder extracted mineral element composition. There was a corresponding relative increase in the level of insoluble (i.e., structural protein) protein in the HSkMC cells when exposed to nutritional drink containing 100 mg extracted mineral element composition. The liquid extracted mineral element composition alone (extracted mineral element composition (Liq. Prep.) also showed stimulation.

As shown in FIG. 2, similar results were obtained when HOb cells were exposed to 1% (v/v) nutritional drink containing extracted mineral element composition for 72 hr. There was a statistically significant increase in metabolic activity as determined using the MTT assay. The relative increase in metabolic activity in HSkMC cells was similar for nutritional drink containing either 100 mg/mL or 200 mg/mL extracted mineral element composition. As illustrated on FIGS. 1 and 2, as little as 100 mg/mL dry extracted mineral element composition powder resulted in a 20% stimulatory effect on cellular metabolism in muscle and bone cells. Furthermore, 100 mg/mL dry extracted mineral element composition powder in the nutritional drink also enhanced by 20% the protein production by muscle cells (FIG. 1). Finally, Totala Liquid alone (liquid preparation of the extracted mineral element composition) also stimulated metabolic activity (by 34-40% as compared with nutritional drink, FIG. 1). The stimulatory effect was statistically significant ($p<0.05$).

Example 3

Bioavailability of an Extracted Mineral Element Composition

Besides basic osmotic role, mineral homeostasis is needed for biochemical reactions in living human or animal bodies. To study the bioavailability of an extracted mineral element composition, human dermal fibroblasts (HDF) were incubated with an extracted mineral element composition and the following characteristics were measured 1) binding of an extracted mineral element composition to cells; 2) intracellular delivery of minerals from an extracted mineral element composition to cells; and 3) intracellular properties of an extracted mineral element composition to cells using cell-permeant mineral-binding dyes—Magnesium Green AM (Mg-Green AM) and Calcein AM.

2. Materials & Methods

Subconfluent pooled adult human dermal fibroblasts (HDF, Cell Applications, San Diego, Calif.) were incubated with a 5% an extracted mineral element composition or with double distilled water for 45 min. followed or not by calcein AM (0.05 μM) or Magnesium Green AM (2.5 μM) loading and rinsing. The fluorescent signal was quantified with Applied BioSystems Cytofluor 4000 fluorometer at ex/em 485/530 nm. For cell observation an inverted Amscope IN300TC-FL epifluorescence microscope with 420-490 nm excitation filter/520 nm cut-off was used, and images were captured with color Discovery 15 CMOS microscope videocamera equipped with ISCapture software. Statistical significance was defined as >10% variation from non-irradiated control and was calculated using double-tailed t-test with p value significance threshold set at 0.05.

3. Results and Discussion

A. The Extracted Mineral Element Composition Associates with Fibroblast Cell Cultures.

The extracted mineral element composition was detected by fluorimetry. When HDF cultures treated with the extracted mineral element composition or water were rinsed and subjected to fluorescence quantification, it was found that the fluorescent signal in extracted mineral element composition-treated cultures was over 10 times higher than the background of water-treated controls (Table XI). Therefore, it can be concluded that the extracted mineral element composition associates with cells or cell membranes, an indication of its bioavailability.

TABLE XI

| Test Material | Fluorescence units |
|---|---|
| $H_2O$ | 3 |
| extracted mineral element composition | 46 |

Fluorescent readings (Ex: 485/40; Gain: 50) of water- and extracted mineral element composition-treated fibroblasts (averaged from at least 6 repeats; $p<0.001$, after rinsing).

B. Intracellular Delivery of a Extracted Mineral Element Composition

TABLE XII

| Test Material | Fluorescence units (Mg-Green AM) |
|---|---|
| $H_2O$ | 399 |
| extracted mineral element composition | 669 |

Fluorescent readings (Ex: 485/40; Em: 530/40; Gain: 50) of water- and 5% extracted mineral element composition-treated fibroblasts (averaged from 3 repeats; $p<0.05$), incubated with the intracellular dye Mg-Green AM. This data indicated that an extracted mineral element composition delivers minerals, such as Mg inside cells, where the minerals are detected by the Mg-Green AM probe, resulting in the increased the fluorescent signal in treated cells.

Magnesium green AM (Mg-Green AM) is a fluorescent indicator binding to a range of ionic minerals. The quantification of fluorescence in fibroblasts incubated with the 5% extracted mineral element composition and compared to the water control showed to an overall increase of ionic mineral content in an extracted mineral element composition composition-treated cells.

C. Activity by Intracellular Extracted Mineral Element Composition

The extracted mineral element composition has activity against cellular components that quench Calcein AM within the cells.

TABLE XIII

| Test Material | Fluorescence units (Calcein AM) |
| --- | --- |
| $H_2O$ | 36 |
| extracted mineral element composition | 67 |

Fluorescent readings (Ex:485/40; Em: 530/40; Gain: 50) of water- and 5% extracted mineral element composition-treated fibroblasts (averaged from 3 repeats; $p<0.05$), incubated with the intracellular dye Calcein AM.

Microscopic observation of the Calcein AM-labeled fibroblasts treated with 5% extracted mineral element composition further confirmed the increase of calcein fluorescence in the extracted mineral element composition-treated cells on a per-cell basis.

Example 4

Hair and Nail Studies

An objective of the present study was to assess the effects of extracted mineral element compositions, MBS Supplement A, MBS Supplement B and MBS Supplement C, on nail condition, specifically nail strength and nail growth. Another objective was to assess the effects of the extracted mineral element compositions on hair and skin condition. Twenty-nine (29) subjects were enrolled and twenty-eight (28) completed the study. One (1) subject was discontinued as a no-show at the time of the final visit. No adverse experiences were reported. MBS Supplement A was the extracted mineral element composition in liquid form. MBS Supplement B was the extracted mineral element composition in liquid form, with flavoring added. MBS Supplement C was water and the flavoring, with no extracted mineral element composition (Control).

In conclusion, under the conditions employed in the study, nails grew as a function of time in all three treatment groups. Percent change as a function of the time was observed to be 142%, 141% and 129% for MBS Supplement A, MBS Supplement B and MBS Supplement C, respectively. Overall, the results indicate the nail plate growth for the small sample was trendwise significantly greater for the MBS Supplement A group than for the MBS Supplement C group. The trend in growth was as follows: MBS Supplement A>MBS Supplement B>MBS Supplement C.

The study was a six (6) week, randomized, double-blind, placebo-controlled evaluation using healthy females with at least ten (10) subjects in each of three extracted mineral element composition percentage groups, which included two (2) test groups and one (1) placebo control group for each concentration. Nail hair and skin condition was evaluated visually by an expert evaluator and subjectively by panelists via self-assessment questionnaires. Nail growth was measured instrumentally using digital photography and subsequent image analysis. Visits occurred at week 0 (baseline) and week six (6). The study protocol was IRB reviewed.

The study inclusion criteria included: 1. Healthy females thirty-five (35) to fifty-four (54) years of age inclusive at enrollment. 2. Self-perceived brittle nails and diminished rate of nail growth as a function of aging. 3. Free of any dermatologic and/or nail disorders that could interfere with evaluation of Supplement performance, and were free of any history of sensitivity to skin treatment products and dietary supplements. 4. Participants understood and were willing to follow study instructions, filled out a brief personal/medical history and signed an informed consent document.

Excluded were: 1. Subjects who were pregnant, breast-feeding, or currently planning a pregnancy. 2. Conditions apparent at entry or recognized after entry that are likely to invalidate a subject's consent to participate in this study and or limit the ability of a subject to regularly attend all study visits or to comply with all other protocol requirements such as: diseases, injuries, alcoholism, drug abuse, psychosis, antagonistic personality, poor motivation, infirmity disability, other problems that may be emotional, intellectual, psychological or social. 3. Other conditions considered by the investigator as sound reasons for disqualification from enrollment into the study. 4. Employees of the testing facility or other testing firms/laboratories, cosmetic or raw goods manufacturers or suppliers.

A. Screening Enrollment and Treatment

Subjects completed a brief medical/personal history and read and signed an informed consent document prior to receiving any study instructions. On the day of the study, a sufficient number of subjects were enrolled, based on enrollment criteria, in order to complete with approximately thirty subjects. Subjects presented at the site without makeup and having washed their faces at least one hour prior to their visit. Subjects underwent a baseline visual evaluation by an experienced IRSI evaluator. Subj ects were considered qualified and were enrolled upon meeting all criteria. The evaluation consisted of examination of the nails, hair, and facial skin condition. After qualifying, subjects then received a subject number. A concept statement (provided by the sponsor), designed to introduce subjects to the technology and history of the Supplement compositions, was shown to subjects prior to study initiation. Subjects then underwent visual and instrumental evaluations and completed a self-administered questionnaire. All findings were documented on the appropriate case report form. Following evaluations, subjects received one (1) of two (2) test Supplements or one (1) control, instructions for use and a diary. Subjects were advised to stop use and inform the laboratory immediately if any problems with nails, hair, skin or Supplement developed. Subjects returned and underwent visual and instrumental evaluations and completed a self-administered questionnaire at week six (6). Upon returning their diaries and any unused test material, each subject received a stipend for her participation and was dismissed from the study. The clinical portion of the study concluded after the dismissal of the last subject from the week 6 visit.

Visual evaluations were made on a continuum scale for the following characteristics:

1. Nail strength, from strong, hard firm to soft, pliable, brittle.

2. Hair

Overall appearance—from excellent to poor

Luster—from shiny, luminous to dull, lifeless

Thickness—from thick, full dense to thin, fine, sparse

Condition—from healthy, well-nourished, moist to damaged, brittle, dry.

3. Facial Skin

Skin texture—from smooth, even surface to rough, coarse, uneven surface

Skin tone—from clear, radiant, translucent to sallow, dull and/or uneven skin

B. Instrumental Evaluations

Subjects equilibrated to interior conditions for at least 15 minutes prior to any instrumental evaluations (photographs with subsequent image analysis). Nails were evaluated using image analysis of digital photographs. Subjects underwent photographic evaluations at baseline and Week 6 visits Image analysis of digital photographs of nails provided a method for quantifying nail augmentation per unit area. For this procedure, a line was etched on the ring and middle fingers of both the right and left hands and photographs/measurements were taken with reference to another mark on the hand/finger such as a line on a knuckle. The lines were etched using a diamond scribe. Image analysis was then conducted on measurement data. Digital photographs were prepared at both the baseline and Week 6 visits. Photographs from all subjects were sent to CuDerm, Inc. for analysis.

Images were taken using a Nikon D70 or D80 camera with a 60 mm micro Nikkor lens set at 1:3 magnification with a modified SB23 Flash Head. Subjects placed their hands on a table against a black background. The camera was mounted on a tripod and directed toward the subjects perpendicularly. Focusing was accomplished using fiber optic focusing lamp. Photographs were taken separately. Images were taken at baseline and week 6.

C. Study Conditions

Subjects were considered in compliance if they missed no more than two doses. The Principal Investigator evaluated compliance on a case-by-case basis if a subject missed more than two doses. Those instances were considered protocol deviations and were documented in the final report.

The Supplement was taken once per day in the morning with breakfast. During the course of the six week study, subjects were not to use: nail products, manicures, nail moisturizers, new nail, hair or skin products, or oral supplements that are specifically designed to improve nails, hair and skin.

D. Study Status

The study enrolled twenty-nine subjects and twenty-eight completed the study. One subject was a no show at the final visit. The age mean ws 46.96.+-0.5.95, all were female, with 23 Caucasian, 3 African American, and 2 Hispanic. Of the twenty-nine subjects, ten were tested with MBS Supplement A, 9 were tested with MBS Supplement B (and one subject dropped out, to result in 8 completing the study), and ten were tested with MBS Supplement C.

E. Results and Discussion

Results of instrumental, visual and subjective questionnaire evaluation of the effects of the test Supplements on nail, hair and skin condition are detailed in Tables XIV through XVII. Mean scores for all parameters were calculated and analyzed for change as a function of time using the Paired Samples t-Test. Test Supplements were compared to the control using the Independent Samples t-Test. In addition, difference scores were also analyzed. Differences scores are defined as the difference between baseline values and each subsequent score and are analyzed in order to compensate for unequal baseline values. Composition-induced change was considered significant at the p.ltoreq.0.050 level.

1. Instrumental Evaluation Nail Growth (Table XIV)

Results of instrumental assessment of nail growth are detailed in Table XIV. Nails grew as a function of time in all three (3) treatment groups. Percent change as a function of time was observed to be 142%, 141% and 129% for MBS Supplement A, MBS Supplement B and MBS Supplement C, respectively. Overall, the results indicate the nail plate growth for the small sample was trendwise significantly greater for the MBS Supplement A group than for the MBS Supplement C group. The trend in growth was as follows: MBS Supplement A>MBS Supplement B>MBS Supplement C.

TABLE XIV

MEAN OVERALL NAIL GROWTH VALUES (mm) ± S.D. (% CHANGE)

| | Supplement A | Supplement B | Supplement C |
|---|---|---|---|
| BASELINE | 1.47 ± 0.46 | 3.83 ± 0.67 | 3.94 ± 0.85 |
| WEEK 6 | 10.09 ± 1.72 | 9.23 ± 1.29 | 9.02 ± 0.56 |
| OVERALL CHANGE (mm) | 5.93 ± 1.50[TBC] (142) | 5.40 ± 0.75 (141) | 5.08 ± 0.56 (129) |

[TBC]Trendwise significantly different than Supplement C based on difference score analysis.

2. Visual Evaluation—Nails Nail Strength (Table XV)

Treatment with MBS Supplement A and MBS Supplement C effected significant increases in mean Nail Strength at week 6 relative to baseline values. In contrast, no significant changes were observed in nail strength with treatment using MBS Supplement B. Comparatively, both MBS Supplement A and MBS Supplement C trendwise outperformed MBS Supplement B.

TABLE XV

MEAN STRENGTH SCORES ± S.D. (% IMPROVEMENT)

| | Supplement A | Supplement B | Supplement C |
|---|---|---|---|
| BASELINE | 7.19 ± 1.28 | 7.18 ± 1.12 | 6.56 ± 1.52 |
| WEEK 6 | 5.97 ± 1.12*[TBD] (17) | 6.90 ± 1.52 (4) | 5.57 ± 1.31*[TBD] (15) |

*Significantly different than baseline value, $p < 0.050$.

[TBD]Trendwise significantly different than Supplement B based on difference score analysis.

3. Visual Evaluation HAIR

Hair—Overall Appearance (Table XVI)

Treatment with MBS Supplement A and MBS Supplement B effected trendwise significant (p=0.150-0.051) and significant increases in mean Hair—Overall Appearance, respectively, at week 6 relative to baseline values. In contrast, no significant changes were observed in Hair Overall Appearance with treatment using MBS Supplement C. Comparatively, no performance differences among Supplements were detected.

Results of Evaluation of the Effects of MBS Supplement A, MBS Supplement B and MBS Supplement C on Hair Condition: Visual Evaluation—Hair Overall Appearance.

TABLE XVI

| MEAN HAIR OVERALL APPEARANCE ± S.D. (% IMPROVEMENT) | | | |
|---|---|---|---|
| | Supplement A | Supplement B | Supplement C |
| BASELINE | 5.73 ± 1.30 | 5.37 ± 1.17 | 5.97 ± 0.90 |
| WEEK 6 | 4.85 ± 1.50$^T$ | 4.82 ± 1.07* | 5.57 ± 1.31 |
| | (15) | (10) | (6) |

*Significantly different than baseline value, p < 0.050.
$^T$Trendwise significantly different than baseline value, p = 0.150-0.051.

Hair Luster (Table XVII)

MBS Supplement B effected a significant increase in Hair Luster, whereas only trendwise significant improvement was observed with MBS Supplement A and MBS Supplement C. Comparatively, no performance differences among Supplements were noted.

TABLE XVII

| MEAN HAIR LUSTER SCORES ± S.D. (% IMPROVEMENT) | | | |
|---|---|---|---|
| | Supplement A | Supplement B | Supplement C |
| BASELINE | 5.63 ± 1.40 | 5.35 ± 1.26 | 5.87 ± 0.82 |
| WEEK 6 | 4.59 ± 1.49$^T$ | 4.56 ± 0.71* | 5.42 ± 0.78$^T$ |
| | (18) | (15) | (8) |

*Significantly different than baseline value, p < 0.050.
$^T$Trendwise significantly different than baseline value, p = 0.150-0.051.

Hair Thickness (Table XVIII)

Treatment with MBS Supplement A resulted in significantly improved Hair Thickness at week 6 as compared to baseline values. No significant changes were noted with MBS Supplement C and MBS Supplement B. Comparatively, MBS Supplement A significantly out-performed MBS Supplement B.

TABLE XVIII

| MEAN HAIR THICKNESS SCORES ± S.D. (% IMPROVEMENT) | | | |
|---|---|---|---|
| | Supplement A | Supplement B | Supplement C |
| BASELINE | 5.24 ± 1.45 | 5.13 ± 1.38 | 6.27 ± 0.87 |
| WEEK 6 | 4.32 ± 1.36*$^{BD}$ | 5.22 ± 1.46 | 5.70 ± 1.50 |
| | (18) | (−2) | (9) |

*Significantly different than baseline value, p < 0.050.
$^{BD}$Trendwise significantly different than Supplement B based on difference score analysis.

Hair Condition (Table XIX)

Trendwise significant improvement in Hair Condition was observed in supplement groups MBS Supplement A and MBS Supplement C, with overall levels of improvement of 14% and 13%, respectively. In contrast, no significant changes in Hair Condition were observed in supplement group MBS Supplement B. Comparatively, MBS Supplement C significantly outperformed MBS Supplement B.

TABLE XIX

| MEAN HAIR CONDITION SCORES ± S.D. (% IMPROVEMENT) | | | |
|---|---|---|---|
| | Supplement A | Supplement B | Supplement C |
| BASELINE | 5.56 ± 1.42 | 5.08 ± 1.45 | 5.82 ± 1.21 |
| WEEK 6 | 4.78 ± 1.25 $^T$ | 5.06 ± 1.36 | 5.09 ± 1.08 $^{T,BD}$ |
| | (14) | (0) | (13) |

* Significantly different than baseline value, p < 0.050.
$^T$ Trendwise significantly different than baseline value, p = 0.150-0.051.
$^{BD}$Trendwise significantly different than Supplement B based on difference score analysis.

4. Visual Evaluation—Skin

Skin Texture (Table XX)

MBS Supplement A effected significant improvement in skin texture at the week 6 assessment interval as compared to baseline, with an overall level of improvement of 33%. In contrast, no significant changes were observed in groups supplemented with either MBS Supplement B, or MBS Supplement C. Comparatively, MBS Supplement A significantly out-performed both Supplement B and MBS Supplement C.

TABLE XX

| MEAN SKIN TEXTURE SCORES ± S.D. (% IMPROVEMENT) | | | |
|---|---|---|---|
| | Supplement A | Supplement B | Supplement C |
| BASELINE | 4.49 ± 1.66 | 3.30 ± 1.65 | 3.74 ± 0.70 |
| WEEK 6 | 3.32 ± 1.45* $^{BD,CD}$ | 3.45 ± 1.34 | 3.89 ± 1.02 |
| | (33) | (−5) | (−4) |

*Significantly different than baseline value, p < 0.050.
$^T$ Trendwise significantly different than baseline value, p = 0.150-0.051.
$^{BD}$ Trendwise significantly different than Supplement B based on difference score analysis.
$^{CD}$Trendwise significantly different than Supplement C based on difference score analysis.

Skin Tone (Table XXI)

No significant changes were observed in skin tone with treatment using MBS Supplement A, MBS Supplement B, or MBS Supplement C.

TABLE XXI

| MEAN SKIN TONE SCORES ± S.D. (% IMPROVEMENT) | | | |
|---|---|---|---|
| | Supplement A | Supplement B | Supplement C |
| BASELINE | 4.04 ± 1.38 | 3.06 ± 1.59 | 3.89 ± 1.22 |
| WEEK 6 | 3.71 ± 1.38 | 3.22 ± 1.30 | 4.05 ± 1.11 |
| | (8) | (−5) | (−4) |

*Significantly different than baseline value, p < 0.050.

5. Subjective Questionnaires (Tables XXII-XXIV)

Supplement A (Table XXII)

Thirty (30) percent of the test subjects reported improvement in nail strength, with a mean level of change of 30%. With respect to hair properties, from 30% to 70% of study participants reported improvement in varying parameters evaluated. Noteworthy, were perceived changes in hair luster and hair condition, where in 60% and 70% of test subjects reported improvement of 43% and 41%, respectively. In addition, improvement in skin texture and tone was also reported, with 30% and 40% of participants reporting levels of improvement of 50% and 39%, respectively.

TABLE XXII

| MEAN FREQUENCY RESPONSE (%) | | | | |
|---|---|---|---|---|
| | YES | NO | UNCERTAIN | % IMPROVEMENT |
| Improved Nail Strength | 3 (30) | 3 (30) | 4 (40) | 30 |
| Improved Hair Appearance | 4 (40) | 4 (40) | 2 (20) | 55 |
| Improved Hair Luster | 6 (60) | 4 (40) | 0 (0) | 43 |
| Improved Hair Thickness | 3 (30) | 4 (40) | 3 (30) | 43 |
| Improved Hair Condition | 7 (70) | 3 (30) | 0 (0) | 41 |
| Improved Skin Texture | 3 (30) | 3 (30) | 4 (40) | 50 |
| Improved Skin Tone | 4 (40) | 4 (40) | 2 (20) | 39 |

* Percent improvement values based on the number of subjects indicating yes.

Supplement B (Table XXIII)

One (1) study participant reported improvement in nail strength, with an overall level of change of 70%. For hair properties, 25% of test subjects reported improvement in varying hair characteristics evaluated. With respect to perceived performance on skin, 25% of participants reported a level of 55% improvement in both skin texture and tone.

TABLE XXIII

| MEAN FREQUENCY RESPONSE (%) | | | | |
|---|---|---|---|---|
| | YES | NO | UNCERTAIN | % IMPROVEMENT |
| Improved Nail Strength | 1 (13) | 5 (63) | 2 (25) | 70 |
| Improved Hair Appearance | 2 (25) | 3 (38) | 3 (38) | 55 |
| Improved Hair Luster | 2 (25) | 3 (38) | 3 (38) | 60 |
| Improved Hair Thickness | 0 (0) | 3 (38) | 3 (38) | 0 |
| Improved Hair Condition | 2 (25) | 3 (38) | 3 (38) | 58 |
| Improved Skin Texture | 2 (25) | 4 (50) | 2 (25) | 55 |
| Improved Skin Tone | 2 (25) | 4 (50) | 2 (25) | 55 |

* Percent improvement values based on the number of subjects indicating yes.

Supplement C (Table XXIV)

Thirty (30) percent of the test subjects reported improvement in nail strength, with a mean level of change of 47%. For hair properties, 10% and 20% of panelists reported improvement of 40% and 30% in hair luster and appearance, respectively. With respect to skin properties, one (1) subject reported improvement in skin tone with an overall level of improvement of 30%.

TABLE XXIV

| MEAN FREQUENCY RESPONSE (%) | | | | |
|---|---|---|---|---|
| | YES | NO | UNCERTAIN | % IMPROVEMENT |
| Improved Nail Strength | 3 (30) | 2 (20) | 5 (50) | 47 |
| Improved Hair Appearance | 2 (20) | 5 (50) | 3 (30) | 30 |
| Improved Hair Luster | 1 (10) | 6 (60) | 3 (30) | 40 |
| Improved Hair Thickness | 0 (0) | 8 (80) | 2 (20) | 0 |
| Improved Hair Condition | 0 (0) | 5 (50) | 5 (50) | 0 |
| Improved Skin Texture | 0 (0) | 5 (50) | 5 (50) | 0 |
| Improved Skin Tone | 1 (10) | 6 (60) | 3 (30) | 30 |

* Percent improvement values based on the number of subjects indicating yes.

CONCLUSION

In conclusion, under the conditions employed in this study, nails grew as a function of time in all three (3) groups. Percent change as a function of time was observed to be 142%, 141% and 129% for MBS Supplement A, MBS Supplement B and MB S Supplement C, respectively. Overall, the results indicate the nail plate growth for the small sample was trendwise significantly greater for the MBS Supplement A group than for the MBS Supplement C group. The trend in growth was as follows: MBS Supplement A>MBS Supplement B>MBS Supplement C.

LIST OF REFERENCES

Aguiar A F, Aguiar D H, Felisberto A D, Carani F R, Milanezi R C, Padovani C R, Dal-Pai-Silva M. Effects of creatine supplementation during resistance training on myosin heavy chain (MHC) expression in rat skeletal muscle fibers. J Strength Cond Res. 2010; 24:88-96.

Balagopal P, Rooyackers O E, Adey D B, Ades P A, Nair K S. Effects of aging on in vivo synthesis of skeletal muscle myosin heavy-chain and sarcoplasmic protein in humans. Am J Physiol. 1997; 273:E790-800.

Balagopal P, Schimke J C, Ades P, Adey D, Nair K S. Age effect on transcript levels and synthesis rate of muscle MHC and response to resistance exercise. Am J Physiol Endocrinol Metab. 2001; 280:E203-8.

Berridge M. V., Tan A. S. Characterization of the cellular reduction of 344,5-dimethylthiazol-2-yl)-2,5-diphenyltetrazolium bromide (MTT): subcellular localization, substrate dependence, and involvement of mitochondrial electron transport in MTT reduction, Arch. Biochem. Biophys. 303:474-482, 1993.

Bruce-Keller A J, Begley J G, Fu W, Butterfield D A, Bredesen D E, Hutchins J B, Hensley K, Mattson M P. Bcl-2 protects isolated plasma and mitochondrial membranes against lipid peroxidation induced by hydrogen peroxide and amyloid β-peptide. J Neurochem. 1998; 70:31-9.

Chen Q, Ames B N. Senescence-like growth arrest induced by hydrogen peroxide in human diploid fibroblast F65 cells. Proc Natl Acad Sci USA. 1994; 91:4130-4.

Deneau J, Ahmed T, Blotsky R, Bojanowski K. Anti-Diabetic Activity of Totala Mineraloid Isolate, In Vitro and in Genetically Diabetic Mice. Int J Vitam Nutr Res., in press.

Distelhorst C W, Lam M, McCormick T S. Oncogene. Bcl-2 inhibits hydrogen peroxide-induced ER Ca2+ pool depletion.1996; 12:2051-5.

Hansen J M, Klass M, Harris C, and Csete M. A reducing redox environment promotes C2C12 myogenesis-implications for regeneration in aged muscle. Cell Biol Int. 2007; 31:546-553.

Nose K, Shibanuma M, Kikuchi K, Kageyama H, Sakiyama S, Kuroki T. Transcriptional activation of early-response genes by hydrogen peroxide in a mouse osteoblastic cell line. Eur J Biochem. 1991; 201:99-106.

Skehan P, Storeng R, Scudiero D, Monks A, McMahon J, Vistica D, Warren J T, Bokesch H, Kenney S, Boyd M R. New colorimetric cytotoxicity assay for anticancer-drug screening. J. Natl. Cancer Inst. 82:1107, 1990.

Tu Y, Xu F H, Liu J, Vescio R, Berenson J, Fady C, Lichtenstein A. Upregulated expression of BCL-2 inmultiple myeloma cells induced by exposure to doxorubicin, etoposide, and hydrogen peroxide. Blood. 1996; 88:1805-12.

Willis D, Moore A R, Frederick R, Willoughby D A. Heme oxygenase: A novel target for the modulation of inflammatory response. Nature Medicine 1996; 2:87-93.

Sequence Listing
<160> NUMBER OF SEQ ID NOS: 22

<210> SEQ ID NO 1
<211> LENGTH: 18
<212> TYPE: DNA
<213> ORGANISM: *Homo sapiens*
<400> SEQUENCE: 1
gagtcaacgg atttggtc <210> SEQ ID NO 2
<211> LENGTH: 23
<212> TYPE: DNA
<213> ORGANISM: *Homo sapiens*
<400> SEQUENCE: 2
caacaatatc cactttacca gag <210> SEQ ID NO 3
<211> LENGTH: 23
<212> TYPE: DNA
<213> ORGANISM: *Homo sapiens*
<400> SEQUENCE: 3
caatctagct aaattccgca age <210> SEQ ID NO 4
<211> LENGTH: 18
<212> TYPE: DNA
<213> ORGANISM: *Homo sapiens*
<400> SEQUENCE: 4
cccatattcc tcggacac <210> SEQ ID NO 5
<211> LENGTH: 19
<212> TYPE: DNA
<213> ORGANISM: *Homo sapiens*
<400> SEQUENCE: 5
tcgtgcctgt ctgattctc <210> SEQ ID NO 6
<211> LENGTH: 20
<212> TYPE: DNA
<213> ORGANISM: *Homo sapiens*
<400> SEQUENCE: 6
gagcagaagg aaagtaatgg <210> SEQ ID NO 7
<211> LENGTH: 20
<212> TYPE: DNA
<213> ORGANISM: *Homo sapiens*
<400> SEQUENCE: 7
ggcctggcct tcttcacctt -continued <210> SEQ ID NO 8
<211> LENGTH: 20
<212> TYPE: DNA
<213> ORGANISM: *Homo sapiens*
<400> SEQUENCE: 8
gcggaagaca gtggtgaact <210> SEQ ID NO 9
<211> LENGTH: 20
<212> TYPE: DNA
<213> ORGANISM: *Homo sapiens*
<400> SEQUENCE: 9
tttcaacaag cccacagggt <210> SEQ ID NO 10
<211> LENGTH: 19
<212> TYPE: DNA
<213> ORGANISM: *Homo sapiens*
<400> SEQUENCE: 10
ccgtcgagac tcctacaac <210> SEQ ID NO 11
<211> LENGTH: 21
<212> TYPE: DNA
<213> ORGANISM: *Homo sapiens*
<400> SEQUENCE: 11
ttctttgagt tcggtggggt c <210> SEQ ID NO 12
<211> LENGTH: 18
<212> TYPE: DNA
<213> ORGANISM: *Homo sapiens*
<400> SEQUENCE: 12
ttgtgagcag cggttcca <210> SEQ ID NO 13
<211> LENGTH: 25
<212> TYPE: DNA
<213> ORGANISM: *Homo sapiens*
<400> SEQUENCE:13
tcacttatga cttttgtgtg aacct <210> SEQ ID NO 14
<211> LENGTH: 21
<212> TYPE: DNA
<213> ORGANISM: *Homo sapiens*
<400> SEQUENCE: 14
tggtgtagaa atactccttg a <210> SEQ ID NO 15
<211> LENGTH: 21
<212> TYPE: DNA
<213> ORGANISM: *Homo sapiens*
<400> SEQUENCE: 15
gattcatgcc cttctctttg g <210> SEQ ID NO 16
<211> LENGTH: 20
<212> TYPE: DNA
<213> ORGANISM: *Homo sapiens*
<400> SEQUENCE: 16
tacaccacaa gccaaacgac <210> SEQ ID NO 17
<211> LENGTH: 20
<212> TYPE: DNA
<213> ORGANISM: *Homo sapiens*
<400> SEQUENCE: 17
gaggggctct ggtccttggt <210> SEQ ID NO 18
<211> LENGTH: 20
<212> TYPE: DNA
<213> ORGANISM: *Homo sapiens*
<400> SEQUENCE: 18
agctggagta gtcgctctgc -continued <210> SEQ ID NO 19
<211> LENGTH: 19
<212> TYPE: DNA
<213> ORGANISM: *Homo sapiens*
<400> SEQUENCE: 19
ggagtctgtc cgtagcacc <210> SEQ ID NO 20
<211> LENGTH: 21
<212> TYPE: DNA
<213> ORGANISM: *Homo sapiens*
<400> SEQUENCE: 20
acactgtctt cacatcaatg c -continued <210> SEQ ID NO 21
<211> LENGTH: 21
<212> TYPE: DNA
<213> ORGANISM: *Homo sapiens*
<400> SEQUENCE: 21
tgcatatttg tttggggcag g <210> SEQ ID NO 22
<211> LENGTH: 221
<212> TYPE: DNA
<213> ORGANISM: *Homo sapiens*
<400> SEQUENCE: 22
ccaacaactg caccgaagag t

SEQUENCE LISTING

<160> NUMBER OF SEQ ID NOS: 22

<210> SEQ ID NO 1
<211> LENGTH: 18
<212> TYPE: DNA
<213> ORGANISM: Homo sapiens

<400> SEQUENCE: 1
gagtcaacgg atttggtc 18

<210> SEQ ID NO 2
<211> LENGTH: 23
<212> TYPE: DNA
<213> ORGANISM: Homo sapiens

<400> SEQUENCE: 2
caacaatatc cactttacca gag 23

<210> SEQ ID NO 3
<211> LENGTH: 23
<212> TYPE: DNA
<213> ORGANISM: Homo sapiens

<400> SEQUENCE: 3
caatctagct aaattccgca agc 23

<210> SEQ ID NO 4
<211> LENGTH: 18
<212> TYPE: DNA
<213> ORGANISM: Homo sapiens

<400> SEQUENCE: 4
cccatattcc tcggacac 18

<210> SEQ ID NO 5
<211> LENGTH: 19
<212> TYPE: DNA
<213> ORGANISM: Homo sapiens

<400> SEQUENCE: 5
tcgtgcctgt ctgattctc 19

<210> SEQ ID NO 6
<211> LENGTH: 20
<212> TYPE: DNA
<213> ORGANISM: Homo sapiens

<400> SEQUENCE: 6
gagcagaagg aaagtaatgg 20

<210> SEQ ID NO 7
<211> LENGTH: 20
<212> TYPE: DNA
<213> ORGANISM: Homo sapiens

<400> SEQUENCE: 7
ggcctggcct tcttcacctt 20

<210> SEQ ID NO 8
<211> LENGTH: 20
<212> TYPE: DNA
<213> ORGANISM: Homo sapiens

<400> SEQUENCE: 8
gcggaagaca gtggtgaact 20

<210> SEQ ID NO 9
<211> LENGTH: 20
<212> TYPE: DNA
<213> ORGANISM: Homo sapiens

<400> SEQUENCE: 9
tttcaacaag cccacagggt 20

<210> SEQ ID NO 10
<211> LENGTH: 19
<212> TYPE: DNA
<213> ORGANISM: Homo sapiens

<400> SEQUENCE: 10
ccgtcgagac tcctacaac 19

<210> SEQ ID NO 11
<211> LENGTH: 21
<212> TYPE: DNA
<213> ORGANISM: Homo sapiens

<400> SEQUENCE: 11
ttctttgagt tcggtggggt c 21

<210> SEQ ID NO 12
<211> LENGTH: 18
<212> TYPE: DNA
<213> ORGANISM: Homo sapiens

<400> SEQUENCE: 12
ttgtgagcag cggttcca 18

<210> SEQ ID NO 13
<211> LENGTH: 25
<212> TYPE: DNA
<213> ORGANISM: Homo sapiens

<400> SEQUENCE: 13
tcacttatga cttttgtgtg aacct 25

<210> SEQ ID NO 14
<211> LENGTH: 21
<212> TYPE: DNA
<213> ORGANISM: Homo sapiens

<400> SEQUENCE: 14
tggtgtagaa atactccttg a 21

<210> SEQ ID NO 15
<211> LENGTH: 21
<212> TYPE: DNA
<213> ORGANISM: Homo sapiens

<400> SEQUENCE: 15
gattcatgcc cttctctttg g 21

<210> SEQ ID NO 16
<211> LENGTH: 20
<212> TYPE: DNA
<213> ORGANISM: Homo sapiens

<400> SEQUENCE: 16
tacaccacaa gccaaacgac 20

<210> SEQ ID NO 17
<211> LENGTH: 20
<212> TYPE: DNA
<213> ORGANISM: Homo sapiens

<400> SEQUENCE: 17
gaggggctct ggtccttggt 20

<210> SEQ ID NO 18
<211> LENGTH: 20
<212> TYPE: DNA
<213> ORGANISM: Homo sapiens

<400> SEQUENCE: 18
agctggagta gtcgctctgc 20

<210> SEQ ID NO 19
<211> LENGTH: 19
<212> TYPE: DNA
<213> ORGANISM: Homo sapiens

<400> SEQUENCE: 19
ggagtctgtc cgtagcacc 19

<210> SEQ ID NO 20
<211> LENGTH: 21
<212> TYPE: DNA
<213> ORGANISM: Homo sapiens

<400> SEQUENCE: 20
acactgtctt cacatcaatg c 21

<210> SEQ ID NO 21
<211> LENGTH: 21
<212> TYPE: DNA
<213> ORGANISM: Homo sapiens

<400> SEQUENCE: 21
tgcatatttg tttggggcag g 21

-continued

```
<210> SEQ ID NO 22
<211> LENGTH: 21
<212> TYPE: DNA
<213> ORGANISM: Homo sapiens

<400> SEQUENCE: 22

ccaacaactg caccgaagag t                                                 21
```

The invention claimed is:

1. A method of slowing an aging process in a human, comprising:

administering to a human having sarcopenia an effective amount of a muscle regenerative composition comprising an extracted mineral element composition, wherein the extracted mineral element composition comprises calcium, chlorine, magnesium, manganese, phosphorous, potassium, silicon, and sodium extracted from at least one of: a clay soil, a mixture of clay soils, and a mixture of clay soils and leonardite; and wherein said administration increases cellular metabolism by at least 20% in the human, thereby reducing muscle degeneration in the human having sarcopenia; and wherein the muscle regenerative composition comprises at least 100 milligrams of the extracted mineral element composition per milliliter of the muscle regenerative composition.

2. The method of claim 1, further comprising inhibiting muscle mass loss or a deleterious change in muscle tone in the human having sarcopenia.

3. The method of claim 1, further comprising modulating a MYH2 gene to upregulate and increase expression of MHCIIa protein by at least 3-fold above a baseline level in at least one muscle cell in the human having sarcopenia, thereby increasing muscle mass in the human having sarcopenia.

4. The method of claim 1, further comprising increasing muscle cell protein production in at least one muscle cell in the human having sarcopenia by about 20%.

5. The method of claim 1, further comprising upregulating gene expression of MYH2 to increase expression of MHCIIa protein by at least 4-fold above a baseline level in at least one muscle cell in the human having sarcopenia, thereby increasing muscle mass in the human having sarcopenia.

6. The method of claim 1 further comprising reversing the free radical-induced suppression of MYH2 expression in at least one muscle cell in the human having sarcopenia; and restoring a pre-senescence production level of MHCIIa protein in the at least one muscle cell.

7. The method of claim 1, wherein the muscle regenerative composition further comprises β-hydroxy-βmethylbutyrate (HMB).

8. The method of claim 1, wherein the muscle regenerative composition is combined with a foodstuff.

9. The method of claim 1, wherein the muscle regenerative composition is combined with a beverage.

10. The method of claim 1, wherein the muscle regenerative composition is combined with a topical.

11. The method of claim 1, wherein the extracted mineral element composition further comprises at least sixty micro mineral elements extracted from at least one of: a clay soil, a mixture of clay soils, and a mixture of clay soils and leonardite.

12. The method of claim 11, wherein the at least sixty micro mineral elements comprise aluminum, antimony, arsenic, barium, beryllium, bismuth, boron, bromine, cadmium, cerium, cesium, chromium, cobalt, copper, dysprosium, erbium, europium, fluorine, gadolinium, gold, hafnium, holmium, iodine, indium, iridium, iron, lanthanum, lead, lithium, lutetium, mercury, molybdenum, neodymium, nickel, niobium, palladium, platinum, praseodymium, rhenium, rhodium, rubidium, ruthenium, samarium, scandium, selenium, silver, strontium, sulfur, tantalum, terbium, tellurium, thallium, thorium, thulium, tin, titanium, tungsten, vanadium, ytterbium, yttrium, zinc, and zirconium.

13. The method of claim 1, wherein the extracted mineral element composition comprises a concentration of the calcium of about 16 mg/ml, a concentration of the chlorine of about 1.7 mg/ml, a concentration of the magnesium of about 2 mg/ml, a concentration of the manganese of about 3 mg/ml, a concentration of the phosphorous of about 0.9 mg/ml, a concentration of the potassium of about 2.4 mg/ml, a concentration of the silicon of about 0.7 mg/ml, and a concentration of the sodium of about 4 mg/ml.

14. The method of claim 1, wherein the extracted mineral element composition comprises a concentration of the calcium of about 8 mg/ml, a concentration of the chlorine of about 0.8 mg/ml, a concentration of the magnesium of about 1 mg/ml, a concentration of the manganese of about 1.5 mg/ml, a concentration of the phosphorous of about 0.43 mg/ml, a concentration of the potassium of about 1.2 mg/ml, a concentration of the silicon of about 0.36 mg/ml, and a concentration of the sodium of about 2 mg/ml.

15. The method of claim 1, wherein the extracted mineral element composition comprises a concentration of the calcium of about 2900 mg/L, a concentration of the chlorine of about 170 mg/L, a concentration of the magnesium of about 460 mg/L, a concentration of the manganese of about 8.6 mg/L, a concentration of the phosphorous of about 200 mg/L, a concentration of the potassium of about 220 mg/L, a concentration of the silicon of about 130 mg/L, and a concentration of the sodium of about 720 mg/L.

16. The method of claim 1, wherein the extracted mineral element composition comprises a weight percent of the calcium of about 8%, a weight percent of the chlorine of about 0.8%, a weight percent of the magnesium of about 1%, a weight percent of the manganese of about 0.002%, a weight percent of the phosphorous of about 0.4%, a weight percent of the potassium of about 1%, a weight percent of the silicon of about 0.4%, and a weight percent of the sodium of about 2%.

17. The method of claim 1, wherein the effective amount of a muscle regenerative composition comprises at least 0.8% calcium, at least 0.08% chlorine, at least 0.1% magnesium, at least 0.0002% manganese, at least 0.04% phosphorous, at least 0.1% potassium, at least 0.04% silicon, and at least 0.2% sodium.

* * * * *